US007666846B2

(12) United States Patent
Ben-Menachem et al.

(10) Patent No.: US 7,666,846 B2
(45) Date of Patent: Feb. 23, 2010

(54) **CHOLESTEROL-CONTAINING COMPOUNDS AND THEIR USE AS IMMUNOGENS AGAINST *BORRELIA BURGDORFERI***

(75) Inventors: Gil Ben-Menachem, Rockville, MD (US); Joanna Kubler-Kielb, Rockville, MD (US); Rachel Schneerson, Bethesda, MD (US); John B. Robbins, Chevy Chase, MD (US); Vince Pozsgay, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 474 days.

(21) Appl. No.: 10/550,907

(22) PCT Filed: Apr. 2, 2004

(86) PCT No.: PCT/US2004/010007

§ 371 (c)(1),
(2), (4) Date: Sep. 27, 2005

(87) PCT Pub. No.: WO2004/089969

PCT Pub. Date: Oct. 21, 2004

(65) Prior Publication Data

US 2006/0204515 A1 Sep. 14, 2006

Related U.S. Application Data

(60) Provisional application No. 60/460,184, filed on Apr. 2, 2003.

(51) Int. Cl.
*A61K 31/70* (2006.01)
*C07J 41/00* (2006.01)

(52) U.S. Cl. .............................. 514/25; 514/26; 536/5; 536/6

(58) Field of Classification Search .................... 536/5, 536/6; 514/25, 26
See application file for complete search history.

(56) References Cited

U.S. PATENT DOCUMENTS 3,966,918 A * 6/1976 Kawamata et al. ............ 514/26
4,031,303 A * 6/1977 Murai et al. .................... 536/5
4,189,471 A * 2/1980 Ponpipom et al. ........ 424/283.1

(Continued)

FOREIGN PATENT DOCUMENTS

EP 0 023 865 A2 2/1981

(Continued)

OTHER PUBLICATIONS

Alving et al., "Antibodies to Cholesterol, Cholesterol Conjugates and Liposomes: Implications for Atherosclerosis and Autoimmunity," *Crit Rev. Immunol.* 10:441-453, 1991.
Anspach, "Endotoxin removal by affinity sorbents," *J. Biochem. Biophys. Methods* 49:665-681, 2001.
Asbrink et al., "The Spirochetal Etiology of Acrodermatitis chronica atrophicans Herxheimer," *Acta Derm Venerol (Stockh)* 64:506-512, 1984.

(Continued)

*Primary Examiner*—Sabiha N. Qazi
(74) *Attorney, Agent, or Firm*—Klarquist Sparkman, LLP

(57) ABSTRACT

Unique compounds that can be used for inducing an immune response to *Borrelia burgdorferi* in a subject by administering a therapeutically effective amount of the glycolipid to the subject. Such administration is particularly useful for preventing or treating Lyme disease in a subject. The compounds(s), and therapeutically acceptable salts thereof, may be formulated into pharmaceutical or immunogenic compositions.

12 Claims, 10 Drawing Sheets

U.S. PATENT DOCUMENTS

| | | | | |
|---|---|---|---|---|
| 4,229,441 | A | * | 10/1980 | Bugianesi et al. ............. 514/24 |
| 4,254,111 | A | * | 3/1981 | Pegel et al. .................... 514/26 |
| 4,721,617 | A | | 1/1988 | Johnson |
| 6,203,798 | B1 | | 3/2001 | Bergstrom et al. |

FOREIGN PATENT DOCUMENTS

| | | |
|---|---|---|
| JP | 08-070885 | 3/1996 |

OTHER PUBLICATIONS

Barbour et al., "Antibodies of Patients with Lyme Disease to Components of the *Ixodes dammini* Spirochete," *The Journal of Clinical Investigation* 72:504-515, 1983.
Barbour et al., "A *Borrelia*-Specific Monoclonal Antibody Binds to a Flagellar Epitope," *Infection and Immunity* 52(5):549-554, 1986.
Barbour et al., "Biology of *Borrelia* Species," *Microbiological Reviews* 50(4):381-400, 1986.
Beck et al., "Chemical and Biological Characterization of a Lipopolysaccharide Extracted From the Lyme Disease Spirochete (*Borrelia burgdorferi*)," *The Journal of Infectious Diseases* 152(1):108-117, 1985.
Beck et al., "Isolation, Preliminary Chemical Characterization, and Biological Activity of *Borrelia burgdorferi* Peptidoglycan," *Biochemical and Biophysical Research Communications* 167(1):89-95, 1990.
Ben-Menachem et al., "Antibody response to MfGL-II, a phosphocholine-containing major lipid of *Mycoplasma fermentans* membranes," *FEMS Microbiology Letters* 154:363-369, 1997.
Bligh et al., "A Rapid Method of Total Lipid Extraction and Purification," *Canadian Journal of Biochemistry and Physiology* 37(8):911-917, 1959.
Bock et al., "A Study of $^{13}$CH Coupling Constants in Pentopyranoses and Some of their Derivatives," *Acta Chemica Scandinavica B* 29(2):258-264, 1975.
Craft et al., "Antigens of *Borrelia burgdorferi* Recognized during Lyme Disease," *J. Clin. Invest.* 78:934-939, 1986.
Dell et al., "F.A.B.-Mass Spectrometry of Carbohydrates," *Advances in Carbohydrate Chemistry and Biochemistry* 45:19-72, 1987.
Habicht et al., "Lyme Disease Spirochetes Induce Human and Murine Interleukin 1 Production," *Journal of Immunology* 134(5):3147-3154, 1985.
Halter et al., "Lipooligosaccharides from *Treponema hyodysenteriae* and *Treponema innocens*," *Infection and Immunity* 56(12):3152-3156, 1988.
Hirai et al., "Unique Cholesteryl Glucosides in *Helicobacter pylori*: Composition and Structural Analysis," *Journal of Bacteriology* 177(18):5327-5333, 1995.
Honarvar et al., "A 14,000 MW lipoprotein and a clycolipid-like structure of *Borrelia burgdorferi* induce proliferation and immunoglobulin production in mouse B cells at high frequencies," *Immunology* 82:389-396, 1994.
Lathrop et al., "Adverse event reports following vaccination for Lyme disease: Dec. 1998-Jul. 2000," *Vaccine* 20:1603-1608, 2002.
Livermore et al., "Lipid Metabolism of *Borrelia hermsi*," *Infection and Immunity* 20(1):215-220, 1978.
Mayberry et al., "Structures and Properties of Acyl Diglucosylcholesterol and Galactofuranosyl Diacylgylcerol from *Acholeplasma axanthum*," *Biochemica et Biophysica Acta* 752:434-443, 1983.
Orloski et al., "Surveillance for Lyme Disease—United States, 1992-1998," *MMWR Morbidity and Mortality Weekly Report CDC Surveillance Summary* 49(SS-3):1-30, 2000.
Paściak et al., "Structure of the major glycolipid from *Rothia dentocariosa*," *Biochimica et Biophysica Acta* 1594:199-205, 2002.
Radolf et al., "Characterization of Outer Membranes Isolated from *Borrelia burgdorferi*, the Lyme Disease Spirochete," *Infection and Immunity* 63(6):2154-2163, 1995.
Rahn, "Vaccine Recommendations: Challenges and Controversies," *Infectious Disease Clinics of North America* 15(1):1-15, 2001.
Rasley et al., "*Borrelia burgdorferi* induces inflammatory mediator production by murine microglia," *Journal of Neuroimmunology* 130:22-31, 2002.
Razin, "Cholesterol Incorporation into Bacterial Membranes," *Journal of Bacteriology* 124(1):570-572, 1975.
Reich et al., "Nuclear Magnetic Resonance Spectrocopy. Carbon-13 Spectra of Steroids," *Journal of the American Chemical Society* 91(26):7445-7454, 1969.
Roth et al., "The Quantitative Determination of Galactose—An Enzymic Method Using Galactose Oxidase, with Applications to Blood and Other Biological Fluids," *Analytical Biochemistry* 10:32-52, 1965.
Rottem, "Sterols and Acylated Proteins in Mycoplasmas," *Biochemical and Biophysical Research Communications* 292(5):1289-1292, 2002.
Sadziene et al., "Experimental Immunization against Lyme Borreliosis with Recombinant Osp Proteins: An Overview," *Infection* 24(2):195-202, 1996.
Sawardeker et al., "Quantitative Determination of Monosaccharides as Their Alditol Acetates by Gas Liquid Chromatography," *Analytical Chemistry* 37:1602-1604, 1965.
Srimal et al., "Titration calorimetric studies to elucidate the specificity of the interactions of polymyxin B with lipopolysaccharides and lipid A," *Biochem. J.* 315 679-686, 1996.
Steere et al., "Chronic Lyme Arthritis. Clinical and Immunogenetic Differentiation from Rheumatoid Arthritis," *Annals of Internal Medicine* 90:896-901, 1979.
Steere et al., "Lyme Carditis: Cardiac Abnormalities of Lyme Disease," *Annals of Internal Medicine* 93(Part1):8-16, 1980.
Steere et al., "The Early Clinical Manifestations of Lyme Disease," *Annals of Internal Medicine* 99:76-82, 1983.
Steere et al., "The Spirochetal Etiology of Lyme Disease," *The New England Journal of Medicine* 308(13):733-740, 1983.
Steere, "Lyme Disease," *The New England Journal of Medicine* 345(2):115-125, 2001.
Takayama et al., "Absence of Lipopolysaccharide in the Lyme Disease Spirochete, *Borrelia burgdorferi*," *Infection and Immunity* 55(9):2311-2313, 1987.
Vinh et al., "Characterization and Taxonomic Significance of Lipopolysacharides of *Leptospira interrogans* Serovar *hardjo*," *Journal of General Microbiology* 135:2663-2673, 1989.
Zähringer et al., "Primary Structure of a New Phosphocholine-containing Glycoglycerolipid of *Mycoplasma fermentans*," *The Journal of Biological Chemistry* 272(42):26262-26270, 1997.
Ben-Menachem et al., "A newly discovered cholesteryl galactoside from *Borrelia burgdorferi*," PNAS 100(13):7913-7918, Jun. 2003.
Cinco et al., "Evidence for (lipo) oligosaccharides in *Borrelia burgdorferi* and their serological specificity," *FEMS Microbiology Immunology* 76:33-38, 1991.
Eiffert et al., "Identification of an immunoreactive non-proteinaleous component in *Borrelia burgdorferi*," *Med Microbiol Immunol* 180:229-237, 1991.
Hossain et al., "Structural analysis of glycolipids from *Borrelia burgdorferi*," *Biochimie* 83:683-692, 2001.
Schröder et al., "Acylated Cholesteryl Galactoside as a Novel Immunogenic Motif in *Borrelia burgdorferi Sensu Stricto*," *The Journal of Biological Chemistry* 278(36):33645-33653 (published electronically Jun. 2003).
Wheeler et al., "Nonprotein Antigens of *Borrelia burgdorferi*," The Journal of Infectious Diseases, 167:665-674, 1993.
International Search Report, International Publication No. WO 2004/089969 A3, published Oct. 21, 2004.
Nishida et al., "One-Pot α-Glycosylation Method Using Appel Agents in *N,N*-Dimethylformamide," *Organic Letters* 5(14):2377-2380, 2003.
Shingu et al., "An easy access to halide ion-catalytic α-glycosylation using carbon tetrabromide and triphenylphosphine as multifunctional reagents," *Org. Biomol. Chem.* 1:2518-2521, 2003.
European Search Report dated Jan. 27, 2009 in European Patent Application No. 08166066.4.

* cited by examiner

FIG. 10
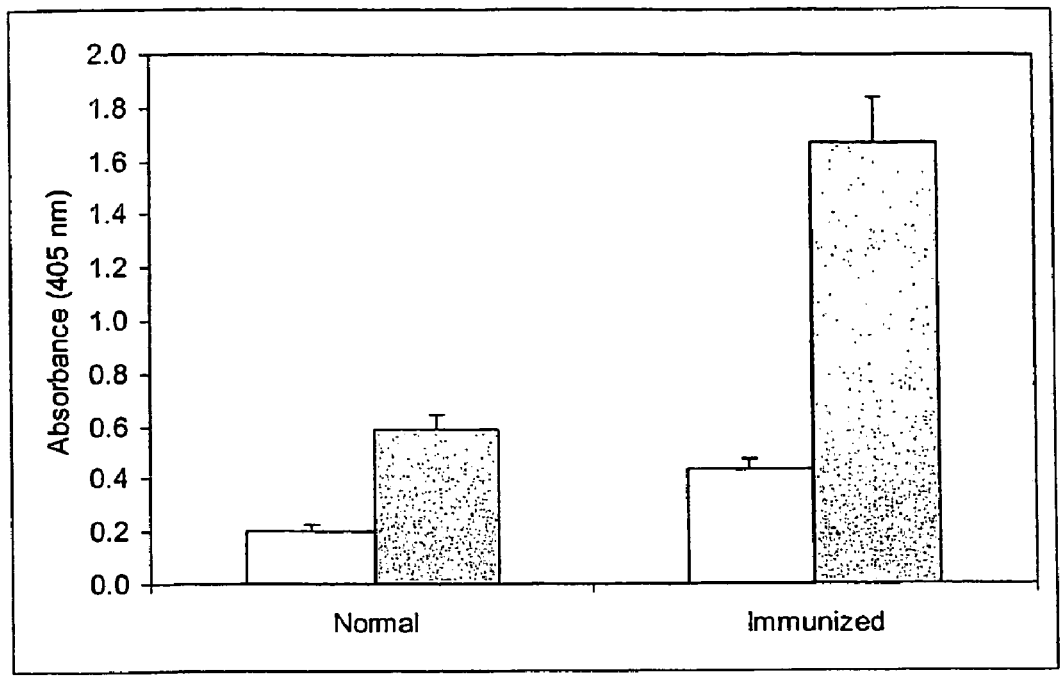
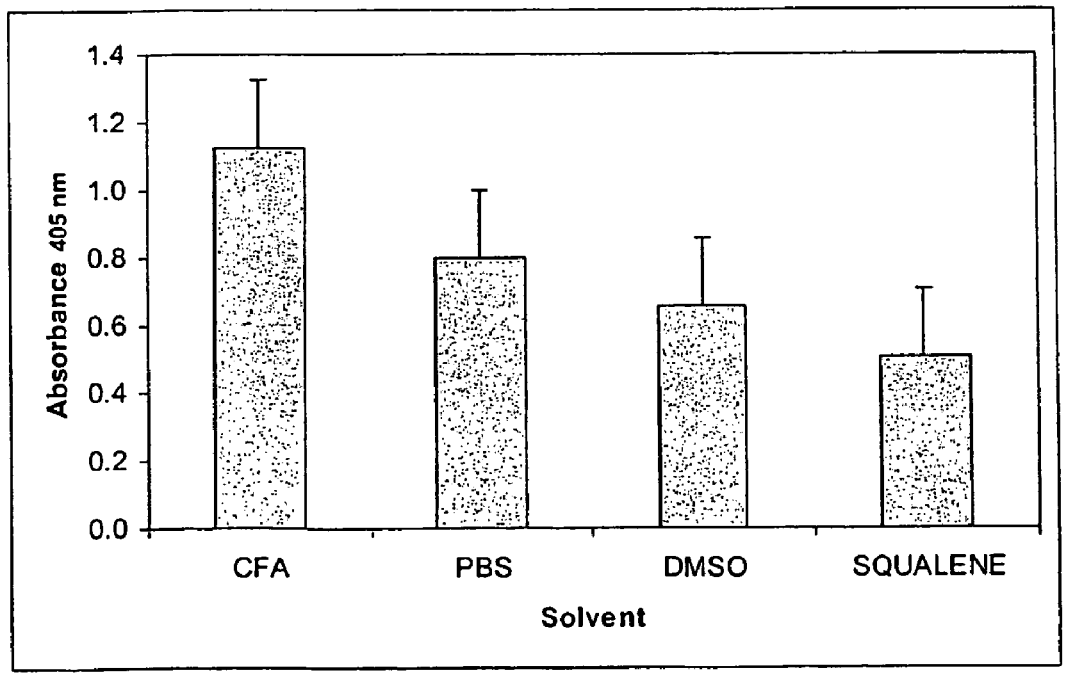
FIG. 11

CHOLESTEROL-CONTAINING COMPOUNDS AND THEIR USE AS IMMUNOGENS AGAINST *BORRELIA BURGDORFERI*

RELATED APPLICATION DATA

This is a §371 U.S. National Stage of International Application No. PCT/US2004/010007, filed Apr. 2, 2004, which was published in English under PCT Article 21(2), which in turn claims the benefit of commonly owned U.S. Provisional Application No. 60/460,184 filed Apr. 2, 2003. These applications are incorporated by reference in their entirety.

FIELD

The disclosure herein relates to the field of cholesterol-containing lipids, and to the use of these cholesterol-containing lipids in producing an immune response against *B. burgdorferi*.

BACKGROUND

Lyme disease is a zoonosis caused by the tick-borne spirochaete *B. burgdorferi* (Steere et al., *N. Engl. J. Med.*, 308: 733-740, 1983). When a susceptible host is bitten by an Ixodes tick, *B. burgdorferi* organisms enter the skin. *B. burgdorferi* spirochaetes are helically shaped, motile cells with an outer cell membrane that surrounds a protoplasmic cylinder complex, consisting of the cytoplasm, the cell wall, the inner cell membrane and the flagella which are located not at the cell surface but in the periplasmic space between the outer cell membrane and the protoplasmic cylinder. The outer cell membrane and the flagella are assumed to play an important role in the host-parasite interactions during the disease and have been subjected to several investigations, identifying major surface-exposed proteins as important immunogens (Barbour et al., *J. Clin. Invest.* 72:504-515, 1983).

In humans the initial skin manifestation is termed erythema chronicum migrans (ECM) whereas a long-standing infection of the skin produces acrodermatitis chronica atrophicans (Asbrink et al., *Acta Derm. Venereol.* 64:506-512, 1984). The *Borrelia* organisms also enter the circulatory system of the host and are distributed to various organs, including the brain and joints (Barbour et al., *Microbiol. Rev.* 50:381-400, 1986). A secondary spread of the pathogens produces a variety of clinical syndromes, including lymphocytic meningoradiculitis (Pfister et al., *J. Neurol.* 118:1-4, 1984), myocarditis (Steere et al., *Ann. Intern. Med.* 93:8-10, 1980) and chronic arthritis (Steere et al., *Ann. Intern. Med.* 90:286-291, 1979). In many patients the infection of some tissues, particularly the brain and joints, persists for years and can be severely disabling. These forms of chronic Lyme disease are a consequence of the host's inability to rid itself of the infectious agent and perhaps the development of an autoimmune reaction (Steere et al., *Ann. Intern. Med.* 99:76-82, 1983).

It has been shown that the earliest IgM antibodies formed against antigens of the *B. burgdorferi* strain B31, which was deposited in the American Type Culture Collection in 1983 with the Accession No. ATCC 35210, are directed against a genus-specific flagellar polypeptide termed flagellin having a molecular weight of 41 kd (Craft et al., *J. Clin. Invest.* 78:934-939, 1986) and which reacts with monoclonal antibody H9724 (Barbour et al., *Infect. Immun.* 52:549-554, 1986). IgG antibodies are also first directed to the 41 kd flagellin, but with advancing disease IgG antibodies form against other immunogens, especially against two abundant proteins with molecular weights of 31 kd and 34 kd. These two proteins, which have been denoted OspA (31 kd) and OspB (34 kd), have been found to be located at the *B. burgdorferi* surface and embedded in its outer fluid cell membrane (Barbour et al., *J. Clin. Invest.* 72:504-515, 1983).

U.S. Pat. No. 4,721,617 discloses the use of inactivated whole *B. burgdorferi* spirochaetes as a vaccine against Lyme disease. In addition, U.S. Pat. No. 6,203,798 teaches the use of protein antigens, OspA and OspB as vaccine candidates. However, as of Feb. 25, 2002, the manufacturer announced that the LYMErix™ Lyme disease vaccine that includes OspA will no longer be commercially available.

Thus, a need remains for a reagent that can be used to produce an immune response against *B. burgdorferi*, such as a protective immune response, in order to produce an effective vaccine to prevent Lyme disease.

SUMMARY

Disclosed herein are unique compounds and their analogs such as therapeutically acceptable salts thereof. According to one aspect, disclosed herein are novel compounds of the following formula A, or a pharmaceutically acceptable salt or complex thereof, wherein $R^1$ is selected from azido, amino, substituted amino, hydrazino (for example, —$NHNH_2$), hydrazide (for example, —$C(O)NHNH_2$), semicarbazide (for example, —$NHC(O)NHNH_2$), or carbohydrazide (for example, —$NHNHC(O)NHNH_2$);

$R^2$ is selected from a saturated or unsaturated carbon chain containing 1 to 25 carbon atoms, particularly 5 to 20 carbon atoms, or a saturated to unsaturated substituted carbon chain containing 1 to 25 carbon atoms, particularly 5 to 20 carbon atoms; and L is selected from O, N, S, P, or an acetylene radical (for example, methylene (—$CH_2$—).

According to another aspect, disclosed herein is a purified compound having a formula B of wherein "16" represents the number of carbon atoms in the straight chain alkyl substituent. This specific, purified compound is referred to herein solely for convenience as "BBGL-II" (i.e., *B. burgdorferi* glycolipid-II).

In a further aspect, disclosed herein are conjugates that include (i) a carrier and (ii) a compound of formula A or B, wherein the compound of formula A or B is bound to the carrier.

The disclosed compounds and conjugates (both of formulae A and B) can be used for inducing an immune response to *B. burgdorferi* in a subject by administering a therapeutically effective amount of the compound or conjugate to the subject. Such administration is particularly useful for preventing or treating Lyme disease in a subject. The compounds(s), and therapeutically acceptable salts thereof, may be formulated into pharmaceutical or immunogenic compositions.

The foregoing and other features and advantages will become more apparent from the following detailed description of several embodiments, which proceeds with reference to the accompanying figures.

BRIEF DESCRIPTION OF THE FIGURES

FIG. 3A is a digital image of CH signals only, obtained by a DEPT-90 experiment. FIG. 3B is a digital image of positive CH$_3$ and negative CH$_2$ resonances computed from DEPT-150-fx DEPT-90, where f is an experimentally adjusted factor.

FIG. 10 is a graph showing antibody titers of sera from rabbits immunized with the glycolipid of formula B. Antibody titers were measured by an ELISA, as described below, and represent an average of four different rabbit sera, diluted 1:100, each tested in three independent assays. Open bars, IgG titers; gray bars, IgM titers; brackets, standard deviation.

FIG. 11 is a graph showing antibody titers of sera from ice immunized with the glycolipid of formula B. Mice (10 mice per group) were immunized as described below, with the glycolipid of formula B in Freund's adjuvant (CFA); PBS; DMSO, or squalene. Antibody titers were determined by an ELISA in sera diluted 1:100, and are represented as an average of three independent assays. Brackets, standard deviation.

DETAILED DESCRIPTION

I. Terms

Figure 1:
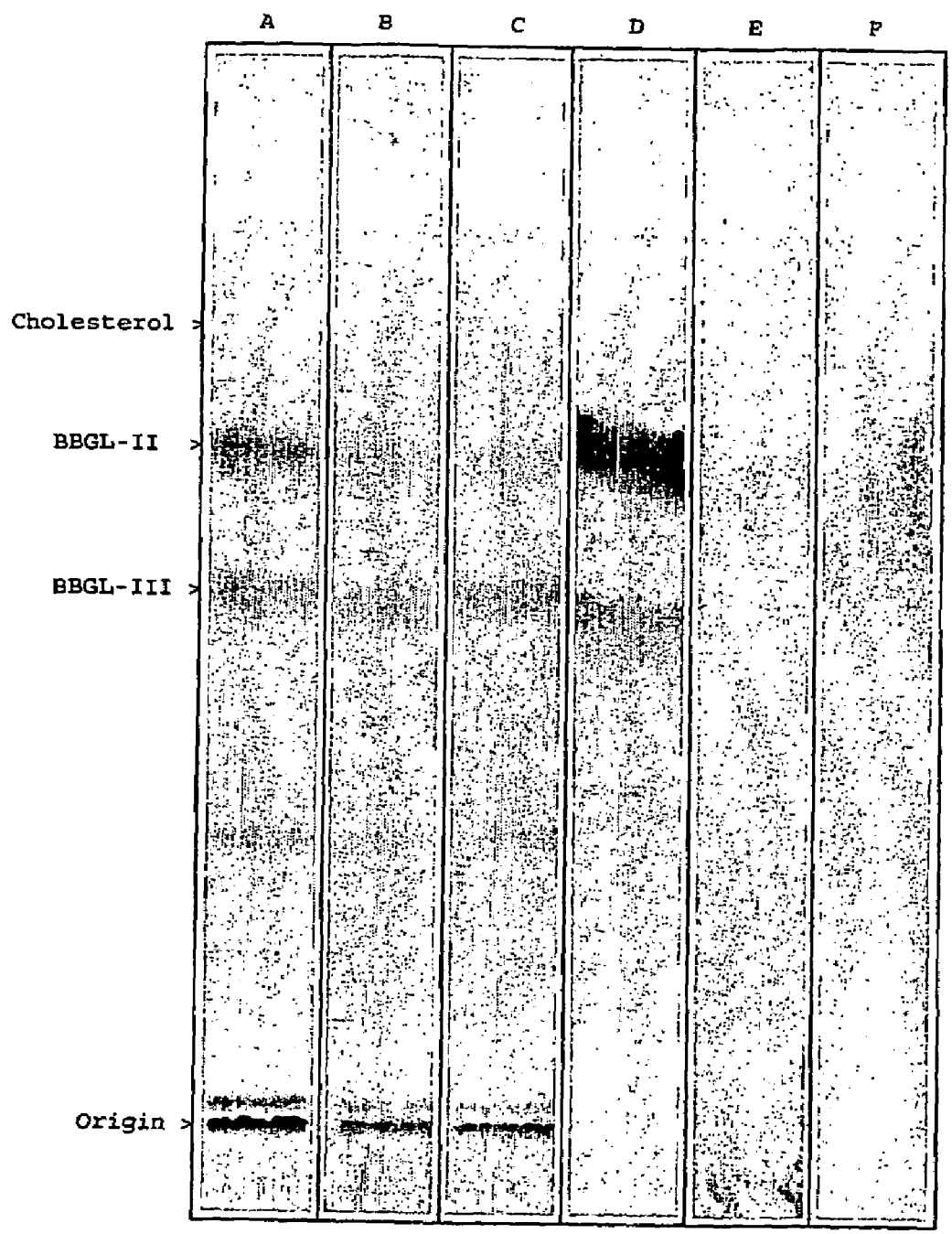
FIG. 1 is a digital image of TLC analysis of lipid extracts from *B. burgdorferi*. Total lipid extracts from strains B31 (lane A), N40 (lane B), and BL303 (lane C) were exposed to iodine vapor, sprayed with anthrone reagent (lane D), and immunostained with mouse anti BBGL-II antiserum (lane E). Alternatively, sonicated B31 cells were loaded onto Detoxi-Gel column, the bound material was eluted with deoxycholate, and the lipids thereof were exposed to iodine vapor (lane F).

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

"Administration of" and "administering a" compound should be understood to mean providing a compound, a pro-drug of a compound, a conjugate of the compound, or a pharmaceutical composition that includes the compound as described herein.

Analog: A molecule, that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacology*, 19$^{th}$ Edition (1995), chapter 28.

Antigen: A compound, composition, or substance that can stimulate an immune response, such as the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-546, 1989) which consists of a VH domain; (v) an isolated complimentarity determining region (CDR); and (vi) a F(ab')$_2$ fragment, a bivalent fragment comprising two Fab fragments linked by a disulfide bridge at the hinge region.

Animal: Living multi-cellular vertebrate organisms, a category that includes, for example, mammals and birds. The term mammal includes both human and non-human mammals. Similarly, the term "subject" includes both human and veterinary subjects.

*Borrelia* (*B.*) *burgdorferi*: A spirochete that was first described by Johnson, et al. in 1984. *B. burgdorferi* can be cultivated from their arthropod vectors or vertebrate hosts in a modified Kelly medium called BSK (Barbour-Stoenner-Kelly). *Borrelia* from ticks and from the blood, skin, and cerebrospinal fluid of Lyme disease patients have been successfully cultivated in BSK. BSK solidified with 1.3% agarose allows the production of colonies from single organisms. *B. burgdorferi* grows slowly as compared to most bacteria. Each spirochete divides into two cells after 12 to 24 hours of elongation. The type of *Borrelia* infecting humans in the U.S. is designated *B. burgdorferi* sensu stricto. *B. burgdorferi* sensu strico and two related *Borrelia, B. garinii* and *B. afzelii* also cause Lyme disease in Europe. In Asia, only *B. garinii* and *B. afzelii* cause Lyme disease in humans.

*Borrelia*, including *B. burgdorferi* are flexible helical cells comprised of a protoplasmic cylinder surrounded by a cell membrane, 7 to 11 periplasmic flagella, and an outer membrane that is loosely associated with the underlying structures. The DNA sequence of *B. burgdorferi* type strain B31 was published in 1997 and contains a 950 kilobase linear chromosome, 9 linear plasmids, and 12 circular plasmids. The outer membrane of *B. burgdorferi* and other *Borrelia* is unique in that genes encoding its proteins are located on linear plasmids; these extrachromasomal genes determine the antigenic identity of these organisms and presumably help the bacteria adapt and survive in ticks and different mammalian hosts.

Conjugate: A "conjugate" is inclusive of any construct that includes an immunogenic compound disclosed herein coupled to a pharmaceutically acceptable carrier. Thus, "conjugate" is not limited to a conjugate of an immunogenic compound covalently bound to a protein carrier (which specific type of conjugate is often referred to in the art as a "conjugate vaccine").

Derivative: A derivative is a biologically active molecule derived from a base molecular structure.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. An "immunogenic composition" is any composition that elicits an immune response in a mammalian host when the immunogenic composition is injected or otherwise introduced. The immune response may be humoral, cellular, or both. A "booster" refers to an increased immune response to an immunogenic composition upon subsequent exposure of the mammalian host to the same immunogenic composition.

Isolated: An "isolated" biological component (such as a lipid) has been substantially separated or purified away from other biological components in the cell of the organism in which the component naturally occurs, i.e., other chromosomal and extra-chromosomal DNA and RNA, proteins, lipids, and organelles. Lipids that have been "isolated" include lipids purified by standard purification methods. The term also embraces lipids and other compounds that are chemically synthesized.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lyme disease: Lyme disease is caused by infection with the bacterium, *Borrelia burgdorferi*. These bacteria are transmitted to humans by the bite of infected deer ticks and cause more than 16,000 infections in the United States each year.

Lyme disease most often presents with a characteristic "bull's-eye" rash, erythema migrans, accompanied by non-specific symptoms such as fever, malaise, fatigue, headache, muscle aches (myalgia), and joint aches (arthralgia).

The incubation period from infection to onset of erythema migrans is typically 7 to 14 days but may be as short as 3 days and as long as 30 days. Some infected individuals have no recognized illness (asymptomatic infection determined by serological testing), or manifest only non-specific symptoms such as fever, headache, fatigue, and myalgia. Lyme disease spirochetes disseminate from the site of the tick bite by cutaneous, lymphatic and blood borne routes. The signs of early disseminated infection usually occur days to weeks after the appearance of a solitary erythema migrans lesion. In addition to multiple (secondary) erythema migrans lesions, early disseminated infection may be manifest as disease of the nervous system, the musculoskeletal system, or the heart. Early neurologic manifestations include lymphocytic meningitis, cranial neuropathy (especially facial nerve palsy), and radiculoneuritis. Musculoskeletal manifestations may include migratory joint and muscle pains with or without objective signs of joint swelling. Cardiac manifestations are rare but may include myocarditis and transient atrioventricular blocks of varying degree. *B. burgdorferi* infection in the untreated or inadequately treated patient may progress to late disseminated disease weeks to months after infection. The most common objective manifestation of late disseminated Lyme disease is intermittent swelling and pain of one or a few joints, usually large, weight-bearing joints such as the knee. Some patients develop chronic axonal polyneuropathy, or encephalopathy, the latter usually manifested by cognitive disorders, sleep disturbance, fatigue, and personality changes. Infrequently, Lyme disease morbidity may be severe, chronic, and disabling. An ill-defined post-Lyme disease syndrome occurs in some persons following treatment for Lyme disease.

Lymphocytes: A type of white blood cell that is involved in the immune defenses of the body. There are two main types of lymphocytes: B cells and T cells.

Pharmaceutically acceptable carriers: A "carrier" is a physiologically acceptable substance with which the therapeutically or biologically active compound disclosed herein is associated. The carrier may facilitate a certain type of administration of the therapeutically or biologically active compound and/or enhance the immune response induced by the therapeutically or biologically active compound. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. *Remington's Pharmaceutical Sciences*, by E. W. Martin, Mack Publishing Co., Easton, Pa., 15th Edition (1975), describes compositions and formulations suitable for pharmaceutical delivery of the BBGL-II herein disclosed.

"Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002).

"Pharmaceutically acceptable complexes" of the presently disclosed estrogenic agents include those complexes or coordination compounds formed from metal ions. Such complexes can include a ligand or chelating agent for bonding with an estrogenic agent.

Polypeptide: Any chain of amino acids, regardless of length or post-translational modification (e.g., glycosylation or phosphorylation).

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a compound preparation is purified such that the lipid disclosed herein represents at least 50%, more particularly at least about 90%, and most particularly at least about 98%, of the total lipid content of the compound preparation.

"Saturated or unsaturated carbon chain" is inclusive of alkyl, alkenyl, alkynyl, alkadienyl or cycloalkyl groups.

"Substituted amino" refers to the group —$NZ^1Z^2$ wherein at least one of $Z^1$ or $Z^2$ is independently selected from alkyl, cycloalkyl, heterocycloalkyl, aryl, heteroaryl, alkoxy, aryloxy, and combinations thereof.

"Substituted carbon chain" refers to a carbon chain in which one or more hydrogen atom of the carbon chain is replaced by another group such as a halogen, aryl, cycloalkyl, amino and combinations thereof.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutically active agent: An agent that causes induction of an immune response, as measured by clinical response (for example increase in a population of immune cells, production of antibody that specifically binds, or measurable resistance to infection with *B. burgdorferi*). Therapeutically active agents can also include organic or other chemical compounds that mimic the effects of BBGL-II.

The above term descriptions are provided solely to aid the reader, and should not be construed to have a scope less than that understood by a person of ordinary skill in the art or as limiting the scope of the appended claims. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for compounds are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. All chemical compounds disclosed herein include both the (+) and (−) stereoisomers (as well as either the (+) or (−) stereoisomer), and any tautomers thereof.

As mentioned above, disclosed herein are biologically active (for example, immunogenic) glycolipids of formula A. These glycolipids are synthetic analogs of BBGL-II in the sense that they are obtained by chemical synthesis as opposed to extraction and purification from *B. burgdorferi*. The compound of formula B, on the other hand, can be obtained by extraction from *B. burgdorferi* (in other words, native BBGL-II).

Native BBGL-II is referred to herein as "cholesteryl 6-O-palmitoyl-β-D-galactopyranoside." The extracted native BBGL-II is isolated and purified. For instance, the purified native BBGL-II isolate is substantially free of other lipids, compounds or molecular fragments from *B. burgdorferi*. In one example, the purified native BBGL-II isolate includes less than one weight percent nucleic acids and less than one weight percent proteins.

Analogs of BBGL-II are also therapeutically useful as disclosed herein (see formula A). For instance, in such an analog the acyl (for example, palmitoyl) group shown for BBGL-II formula may be replaced with other saturated or unsaturated carbon-containing groups or chains containing 1 to 25 carbon atoms, particularly other acyl groups derived from organic fatty acids. The cholesteryl and the galactopyranoside ring structures may include, at any ring position, substituent groups such as alkyl (particularly an acyl group derived from a fatty acid), carboxyl, substituted carboxyl (—COR where R is alkyl or a carboxylic acid or ester), aryl, alkoxy, hetercyclic, halogen, or amino groups. The O heteroatom bridging the cholesteryl and the galactopyranoside rings may be replaced with an alkyl radical (e.g., —CH$_2$—) or a heteroatom such as N, S or P.

In the compounds of formula A, R$^2$ (along with the —C(O)O— group) may be an acyl group derived from an organic fatty acid. Such acyl groups include palmitoyl, lauroyl, stearoyl, myristoyl, oleyl and linoleyl. Derivatization of the acyl group can provide a site (for example, an acyl azide) for covalently bonding to a carrier protein.

In certain variants, the R$^1$ group is capable of forming a covalent bond to a carrier protein (in other words, conjugating to the carrier protein) as described below in more detail. Conjugation to a carrier protein may also be accomplished via derivatization of at least one of the alkyl groups or chains of the cholesteryl moiety. Such derivatization may be accomplished as described below. Alternatively, a small molecule such as adipic dihydrazide or 1,6-diaminohexane may be utilized.

BBGL-II and/or its analogs may be isolated or purified from a *B. burgdorferi* culture as described below, or they can be chemically synthesized. For example, a compound of formula A may be synthesized by first obtaining a galactosyl halide in which the hydroxy groups of the galactose ring have been provided with protecting groups. The galactosyl halide then is reacted with cholesterol to provide a galactosyl-cholesterol. The protective groups on the galactose ring then are removed, and replaced with substitute protective groups. An azidoacyl acid intermediate is prepared separately. The azidoacyl acid intermediate is condensed with the galactosyl-cholesterol to provide an azidoacylated cholesterol β-D-galactopyranoside.

In one example disclosed herein, a therapeutically effective amount of purified, native BBGL-II (formula B) or a chemically synthesized analog of BBGL-II (formula A) is an amount used to generate an immune response, or to treat or prevent infection with *B. burgdorferi* in a subject. Treatment refers to a therapeutic intervention that ameliorates a sign or symptom of *B. burgdorferi* infection, or a sign or symptom of Lyme disease.

Immunogenic Compositions and their Use

In one embodiment, a method of treating a subject with a *B. burgdorferi* infection is provided, or preventing or inhibiting infection, or the development of clinical Lyme disease. Alternatively, the method can be used to inhibit the progress of an already existing infection. The method includes administering to the subject a therapeutically effective amount of a purified native BBGL-II or a compound of formula A, thereby treating or preventing the infection, or retarding or reversing clinical disease. In forming a composition for generating an immune response in a subject, or for vaccinating a subject, BBGL-II or a compound of formula A, is utilized.

These immunogenic compositions of the present disclosure elicit an immune response against *B. burgdorferi* in a mammalian host, including humans and other animals. The immune response may be either a cellular dependent response or an antibody dependent response, or both, and further the response may provide immunological memory or a booster effect or both in the mammalian host. Antigens that elicit antibodies with assistance from T cells are known as T-dependent antigens. Antigens that do not require T cell assistance to elicit antibody formation but can activated B cells directly are known as T-independent antigens. These immunogenic compositions are useful as vaccines and may provide a protective response by the mammalian subject or host to infection by a pathogenic microorganism.

More particularly, the vaccines described herein can be prepared as T-cell independent vaccines and/or as T-cell dependent vaccines. According to a particular variant, the active compound of formula A or B is primarily T-cell independent but is converted into a T-cell dependent response vaccine via conjugation with a carrier (especially a protein carrier).

A carrier may be provided for the compounds of formula A or B disclosed herein. The carrier may exist in an admixture with the immunogenic compound(s), or it may be conjugated to the immunogenic compound(s) via a chemical interaction or bond. For example, the immunogenic compound(s) may be conjugated to a macromolecular carrier. The carrier may be a polymer to which the immunogenic compound(s) is bound by hydrophobic non-covalent interaction, such as a plastic, e.g. polystyrene, or a polymer to which the immunogenic compound(s) is covalently bound, such as a polysaccharide, or a polypeptide, e.g. bovine serum albumin, ovalbumin or keyhole limpet hemocyanin. The carrier should preferably be non-toxic and non-allergenic. The immunogenic compound(s) may be multivalently coupled to the macromolecular carrier as this may provide an increased immunogenicity of the vaccine preparation.

In one embodiment, a carrier is a chain of amino acids (e.g., a polypeptide or protein) or other moieties. In another embodiment, a carrier is a dimer, oligomer, or higher molecular weight polymer of a sequence of amino acids of a *B. burgdorferi* polypeptide. Examples of useful immunogenic carriers include keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

The lipids disclosed herein can be attached to any protein of interest, including, but not limited to, rARU, a recombinant protein containing the repeating units of *Clostridium difficile* toxin A. Carriers are chosen to increase the immunogenicity of the polysaccharide and/or to raise antibodies against the carrier which are medically beneficial. Carriers that fulfill these criteria are described in the art. A polymeric carrier can be a natural or a synthetic material containing one or more functional groups that are available for conjugation, for example primary and/or secondary amino groups, azido groups, aldehydes, hydrazides, epoxides, thiols or carboxyl groups. The carrier can be water soluble or insoluble.

Water soluble peptide carriers are preferred, and include but are not limited to natural or synthetic polypeptides or proteins, such as bovine serum albumin, and bacterial or viral proteins or non-toxic mutants or polypeptide fragments thereof, e.g., tetanus toxin or toxoid, diphtheria toxin or toxoid, *Pseudomonas aeruginosa* exotoxin or toxoid, recombinant *Pseudomonas aeruginosa* exoprotein A, pertussis toxin or toxoid, *Clostridium perfringens* and *Clostridium welchii* exotoxins or toxoids, mutant non-toxic Shiga toxin holotoxin, Shiga toxins 1 and 2, the B subunit of Shiga toxins 1 and 2, and hepatitis B surface antigen and core antigen.

Alternative carriers are some substance, animal, vegetable, or mineral in origin, that is physiologically acceptable and functions to present the BBGL-II lipid to the immune system. Thus, a wide variety of carriers are acceptable, and include materials which are inert, or which have biological activity and/or promote an immune response. For example, an example of a protein carrier includes, but is not limited to, keyhole lympet protein, and hemocyanin. Polysaccharides can also be used as carriers, and include those of molecular weight 10,000 to 1,000,000, such as starches, dextran, agarose, ficoll, or it's carboxyl methyl derivative and carboxy methyl cellulose.

Polyamino acids are also contemplated for use as carriers, and these polyamino acids include, among others, polylysine, polyalanyl polylysine, polyglutamic acid, polyaspartic acid and poly($C_2$-$C_{10}$) amino acids.

Organic polymers can be used as carriers, and these polymers include, for example, polymers and copolymers of amines, amides, olefins, vinyls, esters, acetals, polyamides, carbonates and ethers and the like. Generally speaking, the molecular weight of these polymers will vary dramatically. The polymers can have from two repeating units up to several thousand, e.g., two thousand repeating units. The number of repeating units will be consistent with the use of the immunizing composition in a host animal. Generally speaking, such polymers will have a lower molecular weight, say between 10,000 and 100,000 (the molecular weight being determined by ultracentrifugation).

Inorganic polymers can also be employed. These inorganic polymers can be inorganic polymers containing organic moieties. In particular, silicates and aluminum hydroxide can be used as carriers. It is preferred that the carrier be one which is an immunological adjuvant. In such cases, it is particularly contemplated that the adjuvant be muramyl dipeptide or its analogs.

The carrier can also be the residue of a crosslinking agent employed to interconnect a plurality of synthetic peptide containing chains. Crosslinking agents which have as their functional group an aldehyde (such as glutaraldehyde), carboxyl, amine, amido, imido or azidophenyl group. In particular, there is contemplated the use of butyraldehyde as a crosslinking agent, a divalent imido ester or a carbodiimide.

The present disclosure further includes methods for preparing the immunogenic composition that involves conjugating the lipids disclosed herein to a carrier. Examples of such carrier include those mentioned above as well as a polypeptide or non-peptide moiety that could act as a carrier or adjuvant or have other biological activity in combination with the lipids. The compounds of formula A or B may be conjugated to a protein carrier by mixing the compounds with the protein carrier in the presence of a reagent that allows covalent bond formation between the compound and the protein carrier. Illustrative coupling reagents include glutaraldehyde, hydroxysuccinimides, and carbodiimides. Alternatively, a small chemical molecule may be attached to either the compound of the protein carrier, and this molecule, because of its reactivity, serves as a linker molecule between the compound and the protein carrier. Illustrative linkers include adipic dihydrazide, aminohexanoic acid, chlorohexanol dimethyl acetal, D-glucuronolactone and p-nitrophenyl amine.

For example, the compounds of formula A or B may be conjugated to a polypeptide by one of a number of means, such as by first derivatizing the polypeptide by succinylation and then conjugating the lipid component to the polypeptide through a reaction of the polypeptide and compound with 1, ethyl-3-(3-dimethylaminopropyl)carbodiimide hydrochloride. Additionally the activation of the lipid component can be accomplished by the use of any of several reagents, but preferably cyanogen bromide.

The compounds of formula A or B also may be administered to a subject via a liposome delivery system in order to enhance their stability and/or immunogenicity. Delivery of the compounds via liposomes may be particularly advantageous because the liposome may be internalized by phagocytic cells in the treated subject. Such cells, upon ingesting the liposome, would digest the liposomal membrane and subsequently present the polypeptides to the immune system in conjunction with other molecules required to elicit a strong immune response. The liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154.

The present disclosure involves administering to a subject a therapeutically effective dose of a pharmaceutical composition containing at least one compound of formula A or B. The pharmaceutical composition may include a pharmaceutically acceptable carrier. Administering the pharmaceutical composition of the present invention may be accomplished by any means known to the skilled artisan. By subject is meant any mammal, including a human.

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals. The administration may also be accomplished via a continuous dose for a longer period of time such as, for example, 1-10 weeks.

The pharmaceutical compositions are in general administered orally or parenterally. Parenteral administration routes include, but are not limited to, subcutaneous injections (SQ and depo SQ), intravenous (IV), intramuscular (IM and depo-IM), intrasternal injection or infusion techniques, intranasal (inhalation), intrathecal, transdermal, topical, and ophthalmic. The compound may also be administered from implanted reservoirs or pumps. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science* 249:1527-1533, 1990, which is incorporated herein by reference. Inocula are typically prepared as solutions in physiologically tolerable (acceptable) diluents such as water, saline, phosphate-buffered saline, or the like, to form an aqueous pharmaceutical composition. Adjuvants, such as aluminum hydroxide, may also be included in the compositions.

The pharmaceutical compositions can be administered locally or systemically. Amounts effective for therapeutic use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: The Pharmacological Bases of Therapeutics,* 8th ed., Pergamon Press, 1990; and *Reming-* ton's *Pharmaceutical Sciences,* 17th ed., Mack Publishing Co., Easton, Pa., 1990, each of which is herein incorporated by reference.

Effective doses of the compounds disclosed herein will vary depending on the nature and severity of the condition to be treated, the age and condition of the patient and other clinical factors. Thus, the final determination of the appropriate treatment regimen will be made by the attending clinician. Typically, the dose range for a compound disclosed will be from about 0.1 µg/kg body weight to about 100 mg/kg body weight. Other suitable ranges include doses of from about 1 µg/kg to 10 mg/kg body weight. The dosing schedule may vary from once a week to daily depending on a number of clinical factors, such as the subject's sensitivity to a lipid. In the case of a more aggressive disease it may be preferable to administer doses such as those described above by alternate routes including intravenously or intrathecally. Continuous infusion may also be appropriate.

For administration to animals, purified therapeutically active molecules are generally combined with a pharmaceutically acceptable carrier. Pharmaceutical preparations may contain only one type of therapeutic molecule, or may be composed of a combination of several types of therapeutic molecules. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals may be only inefficiently delivered through ingestion. However, pill-based forms of pharmaceutical proteins may be administered subcutaneously, particularly if formulated in a slow-release composition. Slow-release formulations may be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

The pharmaceutical compositions can be administered by any means that achieve their intended purpose. Amounts and regimens for the administration of the therapeutic molecules can be determined readily by those with ordinary skill in the clinical art of treating Lyme disease and any other condition associated with *B. burgdorferi* infection. For use in treating these conditions, molecules are administered in an amount effective to inhibit *B. burgdorferi* replication. Typical amounts initially administered would be those amounts adequate to achieve tissue concentrations at the site of action which have been found to achieve the desired effect in vitro. The compounds of formula A or B can be administered to a host in vivo, for example through systemic administration, such as intravenous or intraperitoneal administration. Also, the compounds of formula A or B can be administered intralesionally: i.e., the peptide or protein is injected directly into the lesion. In order to increase the immune response, a subsequent or booster dose may be administered approximately 4 to 6 weeks after the initial injection. Subsequent doses may be administered as indicated herein, or as desired by the practitioner.

The disclosure is illustrated by the following non-limiting Examples.

EXAMPLES

Example 1

Materials and Methods

Organism and Growth Conditions—*B. burgdorferi* strains B31 (ATCC 35210), BL303 and N40 were cultivated in BSK-H medium (Sigma). Media were inoculated with 2% (vol.) of a frozen culture and incubated statically at 37° C. for 72 hours to the mid-exponential phase of growth (pH 7.0). Cells were harvested by centrifugation at 12,000 g for 30 minutes, washed three times with cold PBS and kept at −20° C. until used.

Lipid Extraction and Analyses—Lipids were extracted from washed cells by the method of Bligh and Dyer (14). The chloroform phase was evaporated using a rotary evaporator, followed by a stream of nitrogen, and the dried lipids (0.1-0.2 mg/ml cell protein) were redissolved in 1-2 ml chloroform. Quantitative separation of BBGLs was achieved by silica gel column chromatography. Total lipid extract (10 mg) in 5 ml chloroform was loaded onto a silica gel column (20×3 cm, Kieselgel 60, Merk, 230400 mesh) that was sequentially eluted with 10 bed volumes of chloroform (fraction 1); 2.5% methanol:chloroform (vol:vol; fraction 2); 5% methanol:chloroform (vol:vol; fraction 3), 10% methanol:chloroform (vol:vol; fraction 4) and methanol (fraction 5). The fractions were evaporated to dryness in a rotary evaporator, and a stream of nitrogen, redissolved in 1 ml chloroform and kept at −20° C. Fraction 3 contained almost exclusively BBGL-II, whereas fraction 4 contained BBGL-III. For qualitative lipid analysis the total lipid fraction (20 µl containing 200 µg) was chromatographed on silica gel HR-coated aluminum plates (Merck, Darmstadt, Germany) and developed using chloroform:methanol (9:1 by vol.). Lipid spots were detected by iodine vapor, and glycolipids were detected by anthrone spray reagent.

Radiolabeling—Cholesterol labeling of *B. burgdorferi* was performed by adding [4-$^{14}$C]cholesterol (Amersham Pharmacia, GB, courtesy of W. Prinz, NIDDK, NIH) to 100 ml media at the time of inoculation. Labeled cholesterol (specific activity 58.0 mCi/mmol) was added at 0.1 µCi/ml in a mixture of Tween 80:Ethanol (1:1 by vol.) at final volume of 50 µl. Lipid extraction was performed as mentioned. For determining radioactivity in the lipid spots, total lipids were separated on TLC plates, the plates were then shortly exposed to iodine vapor, and the spots were scraped off into scintillation chamber containing 1 ml of scintillation liquid. Radioactivity was measured in a Perkin Elmer scintillation counter (model 1450 microbeta) and expressed as decompositions per min (dpm).

Affinity Chromatography—BBGL-II was also purified by affinity chromatography using Detoxi-Gel Endotoxin Removing Gel (Pierce, Rockford, Ill.). *Borrelia* cells were washed 5 times with PBS, resuspended in the same buffer, and disrupted by ultrasonic treatment for 30 seconds, in a Branson sonifier operated at 50% duty cycles at 100 W. Membranes were separated from the soluble fraction by centrifugation at 37000 g for 30 minutes, and the supernatant (1 ml containing 1 mg total protein) was loaded on a detoxi-gel (agarose-immobilized-polymixin B) column (0.9×10 cm).

The column was washed with 10 bed-volumes of PBS. Elution of the bound material was performed by washing with 10 bed volumes of PBS containing 1% Deoxycholic acid (w/v), according to the manufacturer's instructions. The bound fraction was dialyzed against distilled water, lyophilized, and lipids were extracted as mentioned.

Immunization and Immunostaining—Groups of ten female NIH Swiss albino mice (5-6 weeks old, general purpose) were immunized intraperitoneally with 2 doses of BBGL-II emulsified in complete Freund's adjuvant (first dose) or incomplete Freund's adjuvant (second dose) two weeks apart. The doses contained 10 µg BBGL-II per 0.1 ml and were administered IP in 0.1 ml. Alternatively, mice were immunized three times, 2 weeks apart, with 10 µg of BBGL-II emulsified in 0.1 ml of DMSO, squalene, or PBS. Mice were bled 2 weeks after the second dose and the sera thus obtained was kept at −20° C. until used. Rabbits (females, New Zealand White, 8 weeks old) were immunized with two doses of BBGL-II, 75 µg each, in Fruend's adjuvant, administered i.m. and i.c. in 20×0.05 ml.

Immunostaining of membrane lipids was performed as previously described (15). Developed chromatogram plates, containing lipid spots, were coated with polyisobutyl-methacrylate solution (0.05% in hexane) and allowed to dry. The plates were then blocked with PBS containing 1% BSA and 0.05% tween 20 for 15 minutes, and then incubated with anti BBGL-II antiserum, diluted 1:100 in PBS-BSA buffer for 1 hour at 22° C. The plates were rinsed 5 times with PBS-BSA buffer and incubated with alkaline phosphatase-conjugated rat anti mouse IgG (KPL, MD) diluted 1:25,000 in PBS-BSA for 1 hour at 22° C. The plates were then washed, and developed using BCIP/NBT (KPL, MD).

Analytical Methods—Sugar analysis was carried out according to Sawardeker et al (16). In brief, 0.5 mg of BBGL-II or BBGL-III were hydrolyzed in 1 M HCl for 4 hour in 100° C. and, after reduction and peracetylation, analyzed by GLC-MS using Hewlett-Packard apparatus (model HP 6890) with a type HP-5 glass capillary column (0.32 mm by 30 minutes) and temperature programming at 8° C./minute, from 125-250° C. in the electron ionization (106 eV) mode. Fatty acids were analyzed after methanolysis of dried glycolipids with 1 M HCl/MeOH for 5 hours in 80° C. The solvent was removed under a stream of nitrogen and the free fatty acid methyl esters were extracted with chloroform. Analysis was carried out with GLC-MS under the conditions described above.

Double Bond Localization—The position of double bond in unsaturated fatty acids was performed by GLC-MS after 4,4-dimethyloxazoline derivatization (17). Chloroform phase was dried under a stream of nitrogen, then mixed with 500 µl of 2-amino-2-methylpropanol and heated overnight at 150° C. After cooling, the reaction mixture was dissolved in 3 ml of dichloromethane and washed twice with 2 ml of distilled water.

Methylation Analysis—Native and O-deacylated glycolipid were methylated according to (18). The methylated products were hydrolyzed with 1 M HCl for 4 hours in 100° C., converted to alditol acetates and analyzed with GLC-MS.

O-Deacylation—Glycolipids (2 mg) were O-deacylated with 0.33 ml of 0.25 M $NaOCH_3$ in methanol at 37° C. The reaction was monitored by TLC. After 2 hours no spots accounting for the original, unmodified glycolipids were found. Solvents were evaporated under a stream of nitrogen and the products were extracted with chloroform water (1:1 by vol.). Both organic and inorganic phases were analyzed for sugar and fatty acids by GLC-MS.

Determination of Absolute Configuration—BBGL-II was hydrolyzed with 1 M HCl at 100° C. for 4 hours. D-Galactose was quantified from the dried neutralized sample by the enzymatic method using galactose oxidase (19). Determination of the absolute configuration of glycerol was performed according to (1) with prior O-deacylation of the glycolipid (20). In this method the primary hydroxyl group of glycerol, released after saponification of the glycolipid, is oxidized by TEMPO and transformed into a glyceric acid residue. After acid hydrolysis the glyceric acid was esterified with (R)-(−)-2-butanol, acetylated and analyzed with GLC-MS. The retention time was compared to the authentic samples obtain from D- and L-glyceric acid.

FAB Mass Spectrometry—The mass spectra were recorded using 6 keV atoms to ionize samples from 3-nitrobenzyl alcohol or glycerol as the matrix. Peracetylation of the samples were done as described by Dell (21).

Matrix-assisted Laser Desorption/Ionization Time-of-Flight Mass Spectrometry (MALDI-TOF)—Mass spectra were obtained using a PerSeptive BioSystems Voyager Elite DE-STR (PE-Biosystems, Framingham, Mass.) MALDI-TOF instrument. Mass spectra were accumulated for 100 laser shots at an attenuation of 2600. The instrument was operated in the linear mode with 20 kV accelerating voltage and a 150 nsec ion extraction delay time. Sample and Matrix were prepared as described previously (22). In brief, BBGL-II and BBGL-III were dissolved in chloroform:methanol (1:1 by vol) to a concentration of 4 µg/µL and applied as 0.5 µL droplets to separate positions in the center of the multiple sample plate. An equal volume of matrix, 2,5-dihydroxybenzoic acid, 10 mg/mL water was applied over each sample and dried before being inserted into the mass spectrometer.

NMR spectroscopy—Monogalactosyl diglyceride (MGDG, mainly 1,2-di-O-stearoyl-3-O-β-D-galactopyranosyl glycerol) was obtained from Matreya, State College, Pa. 1,2-Di-O-palmitoyl glycerol (1,2-dipalmitin) was obtained from NuChek, New Elysian, Minn. Methyl α-D-galactopyranoside was prepared in-house, and methyl β-D-galactopyranoside was obtained from Aldrich, Milwaukee, Wis. Deuterated solvents were purchased from Cambridge Isotope Laboratories, Andover, Mass.

NMR spectra were acquired at 300 K without spinning, by use of a Bruker DRX-500 spectrometer equipped with a 5 mm broad band (BBO) probe. Solutions of 5-10 mg of compound in $CDCl_3$ (0.5 mL, 99.96 atom % D) or its admixtures with $(CD_3)_2CO$ (99.9 atom % D) or $CD_3OD$ (99.8 atom % D) were used for the lipids, with tetramethylsilane as a chemical shift reference for $^1H$ and $^{13}C$ NMR spectra. The anomeric methyl D-galactopyranosides (11 mg) were examined as their solutions in $D_2O$ (0.4 mL, 99.96 atom % D), with sodium 4,4-dimethyl-silapentanoate-2,2,3,3-$d_4$ (TSP) as an internal reference for $^1H$ and $^{13}C$ NMR spectra. The data were acquired and processed by means of the Bruker XWINNMR program version 3.0, running on SGI O2 or Octane 2 processors. 32,768 point data sets were used for 1D spectra, in some instances with zero-filling to 32,768 or 65,536 points. 1D $^1H$ NMR spectra were recorded at 500 MHz with a spectral width of 4.25 kHz, a 30° pulse (3.2 µs), and a recycle time of 6 s. 1D $^{13}C$ NMR spectra were acquired at 126 MHz by using a spectral width of 25.1 kHz, a 45° pulse (3 µs), and a recycle time of 1 s, except that for high resolution studies of closely spaced $^{13}C$ resonances of cholesterol, 65,536 point data sets were used, with zero-filling to 131,072 points. 1D $^{13}C$ NMR spectrum editing was conducted by the DEPT method, using combinations of spectra acquired with 30°, 90°, and 150° read pulses at the $^1H$ frequency. In other cases, a 135° $^1H$ read pulse was used to generate $^{13}C$ NMR spectra having negatively phased $CH_2$ resonances, together with positively phased CH and $CH_3$ resonances. $^1H$ coupled $^{13}C$ NMR spectra were acquired with the nuclear Overhauser effect by use of gated irradiation at the $^1$H frequency during a relaxation delay of 3.42 s.

Most of the 2D NMR data were acquired by means of pulse sequences that included z-gradient coherence selection.

2D COSY $^1$H NMR spectra were collected in 2048×512 point data sets, zero-filled to 2048×2048 points, using either 30° or 45° read pulses. Unshifted sine-bell squared window functions were applied in both dimensions prior to Fourier transformation, after which the frequency data were displayed in magnitude mode. 2D TOCSY $^1$H NMR spectra were acquired using 16384×256 point data sets, zero-filled to 16384×2048 points, by use of the gradient-selected, phase sensitive, echo/anti-echo protocol. Sine-bell squared windows shifted by $\pi/2$ rad were applied in both dimensions. 1D $^1$H NMR subspectra of individual residues were produced by extraction of $F_2$ slices from the 2D TOCSY spectra. For some $^1$H NMR spectra, the assignments were also confirmed by digital, selective homonuclear $^1$H decoupling.

2D HSQC and HMBC $^1$H/$^{13}$C NMR spectra were recorded as 2048×512 point data sets, zero-filled to 2048×2048 points, by using the gradient-selected, sensitivity-enhanced, phase-sensitive echo/anti-echo mode for HSQC, and a gradient-selected, low-pass filtered, long-range, non-decoupled pulse sequence for HMBC, the data from which were displayed in magnitude mode. 2D HMBC NMR spectra were acquired with an evolution delay of 83 ms, i.e., optimized for $^{2,3}J_{CH}$ 6.0 Hz. Optimum sensitivity was obtained for the HSQC and HMBC spectra by use of sine-bell squared window functions shifted by $\pi/2$ rad in both dimensions. Ridges in the $t_1$ dimension of the 2D spectra were removed as necessary by mean row subtraction in the Bruker AURELIA program, version 2.8.12. $^{31}$P NMR measurements at 202 MHz indicated the absence of phosphorus in the samples examined.

Example 2

Isolation of BBGL-II and BBGL-III

The glycolipids of *B. burgdorferi* (strain B31) were obtained from 2.17 g of dry cells after Bligh and Dyer extraction. They were purified to homogeneity by silica gel column (20×3 cm) and eluted stepwise with mixtures of chloroform and methanol with increasing polarity. The yield of BBGL-II from 0.7 g total lipids was 163 mg (23.2%) and the yield for BBGL-III was 87 mg (12.4%), thus BBGL-II and BBGL-III are the major lipids in *B. burgdorferi*. Similar yields were obtained from the clinically isolated strains BL303 and N40, which lipids repertoire resembled that of B31 strain (FIG. 1). Since the biomass yields from B31 strain were much higher, all subsequent experiments were performed with this strain.

Example 3

Affinity Chromatography

BBGL-II bound to Detoxi-Gel Endotoxin Removing Gel (Pierce). This resin consists of immobilized polymixin B on agarose, and is used for the removal of endotoxins by binding to the lipid A portion of LPS. When sonicated *B. burgdorferi* cells were loaded on this column, the presence of BBGL-II in the bound material, eluted from the column with 1% deoxycholic acid, could be demonstrated by TLC as well as by immunolabeling (FIG. 1). No presence of BBGL-II was detected in the bound fraction.

Example 4

Radioactive Labeling of BBGL-II

When cultivated in the presence of $^{14}$C-cholesterol, 80% of the radioactivity found in the total lipid extract could be attributed to BBGL-II (Table 1). No radioactivity was detected in lipid bands corresponding to BBGL-III, free cholesterol or cholesterol esters.

TABLE I

The chemical composition of *B. burgdorferi* glycolipids.

| Component | BBGL-II | | BBGL-III | |
|---|---|---|---|---|
| | Native | O-deacylated | Native | O-deacylated |
| Sugar[a] | | | | |
| Galactose | 1.0 | 1.0 | 1.0 | 1.0 |
| Glycerol | 0 | 0 | 0.93 | 1.05 |
| Fatty acids[a] | | | | |
| C 14:0 | 0.07 | | 0.15 | |
| C 16:0 | 1.15 | | 1.00 | |
| C18:2 (9, 12)[b] | 0.23 | | 0.12 | |
| C18:1 (9)[b] | 1.0 | | 0.65 | |
| C18:0 | 0.16 | | 0.25 | |
| $^{14}$C-Cholesterol[c] | 79.3% | ND | 0.4% | ND |

[a]Molar ratio was determined by GLC-MS
[b]Localization of the double bond
[c]Relative amount of radioactivity labeling out of the total lipid fraction (see Example 1 for details)

Example 5

Compositional Analysis

Sugar analysis of both glycolipids revealed the presence of galactose as the only monosaccharide. Glycerol was detected only in BBGL-III. Methanolysis identified the presence of two major ester-bound fatty acids: C16:0 and C18:1 and several minor fatty acids: C14:0, C18:0 C18:2 (Table 1). The double bond was localized on position $\Delta 9$ and $\Delta 9,12$ in C18:1 and C18:2 respectively, suggesting these fatty acids are oleic and linoleic acids.

Enzymatic assay with galactose oxidase demonstrated the galactose moiety to be in the D configuration. Absolute configuration of the carbon on position C-2 in the glycerol moiety of BBGL-III, with the sugar residue on position C-3 and the fatty acid on positions C-1 and C-2, was determined to be L. This is consistent with sn-configuration when carbons are stereospecifically numbered.

Example 6

Methylation Analysis

Methylation analysis of the native BBGL-II, revealed the presence of 1,5-di-o-acetyl-2,3,4,6-tetra-O-methyl-galacitol and 1,5,6-tri-O-acetyl 2,3,4-tetra-methyl-galacitol in the molar ratio of 1.0 to 0.9, identifying terminal and 6-substituted galactose residues. Prior de-O-acylation of the sample resulted in the disappearance of the 6-substituted galactose and the terminal galactose was the only detected component. This suggests that the fatty acid chain, which is not completely removed during methylation performed according to (23), is located in position C6 of the galactose. Methylation analysis of BBGL-III detected 1,5-di-o-acetyl-2,3,4,6-tetra-O-methyl-galacitol indicating the presence of terminal galactose.

Example 7

Mass Spectroscopy

Figure 2:
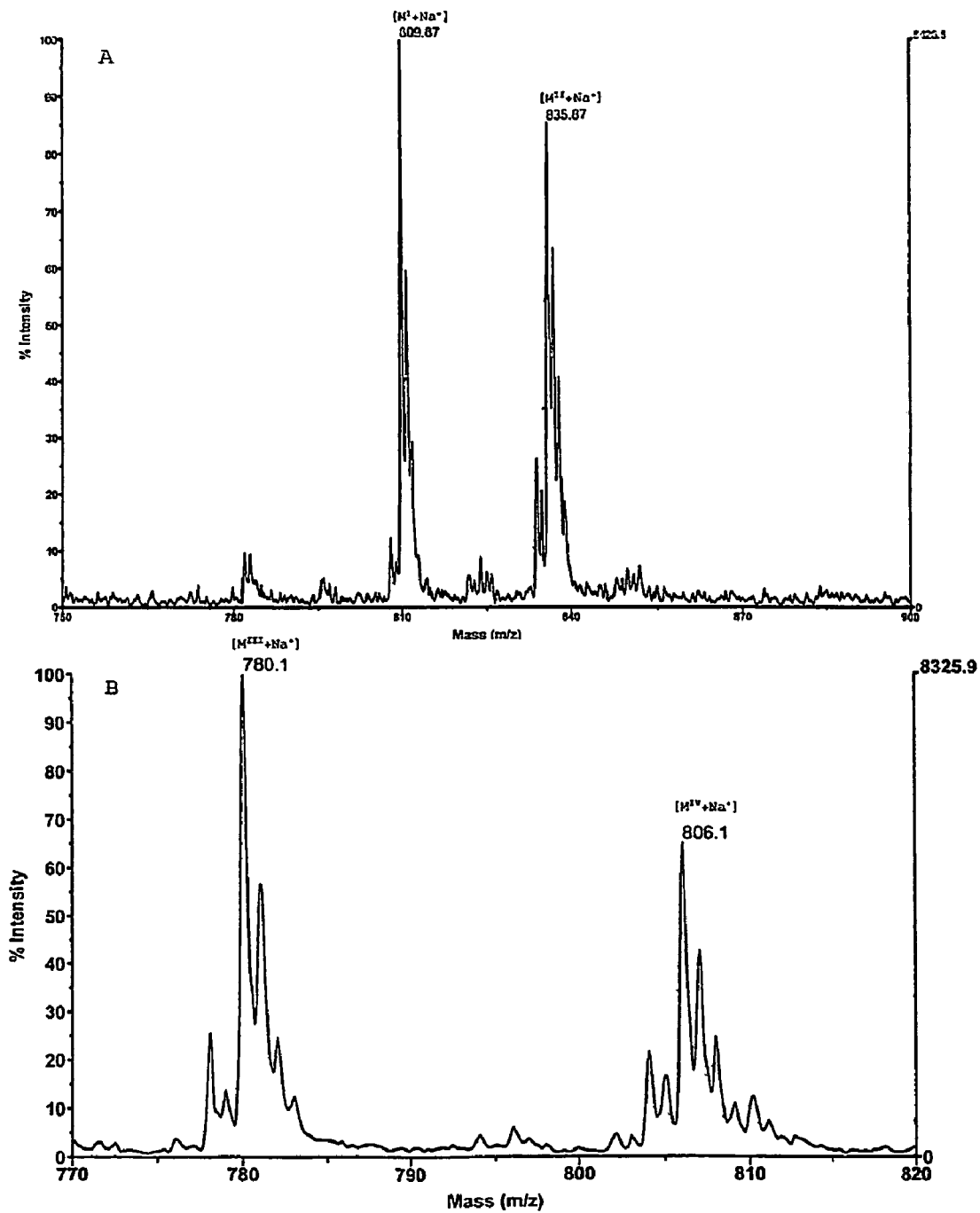
FIG. 2 is a digital image of part of the MALDI-TOF mass-spectra of sodium adduct of BBGL-II and BBGL-III. Two major peaks of pseudomolecular ions [M+Na$^+$] at m/z 809.87 and 835.87 represent cholesteryl galactose with palmitic (M$^I$) and oleic (M$^{II}$) derivatives of BBGL-II (A), and pseudomolecular ions [M+Na]$^+$ at m/z 780.1 and 806.1 represent monogalactosyl diacyl glycerol (BBGL-III) substituted with dipalmitoyl (M$^{III}$) and palmitoyl-oleyl (M$^{IV}$) derivatives (B).

MALDI-TOF spectra of BBGL-II, recorded in the positive ion mode, detected two molecular sizes of 810.1 and 836.1. The difference between the molecular weights ($\Delta$m/z=26) suggested variability in the lipid component, representing the sodium adduct of cholesteryl galactose substituted with either palmitic or oleatic fatty acids (FIG. 2). This is in agreement with results obtained by GLC-MS, which showed these fatty acids as the predominant moieties. FAB-MS analysis of native BBGL-II detected molecular masses of 809.7 and 835.7, whereas analysis of peracetylated BBGL-II detected molecular weights of 935.7 and 961.7. The increase in molecular weight of $\Delta$m/z=126 represents the incorporation of three acetyl groups, and confirmed the existence of three free hydroxyl groups in BBGL-II. To confirm the composition BBGL-II, high resolution FAB-MS was recorded. The theoretical m/z value of the cesium adduct of the compound, composed of hexose, cholesterol and oleic acid ($C_{51}H_{86}O_7Cs$), was calculated to be 943.5428. The observed m/z weight was 943.5469. This confirmed the theoretical composition $C_{51}H_{86}O_7Cs$ (error [ppm/mmu]=+4.3/+4.1).

MALDI-TOF spectra of BBGL-III revealed two ions with masses of 780.1 and 806.1 which accounted for sodium adducts of monogalactosyl diacyl glycerol with two 16:0 fatty acids or with 16:0 and 18:1 fatty acids respectively (FIG. 2).

Example 8

NMR Spectroscopy

The structures of the BBGL-II and BBGL-III and their peracetyl derivatives were investigated further by one-dimensional (1D) and two-dimensional (2D) NMR spectroscopy at 500 MHz. $^1$H NMR assignments (Table II) were confirmed by 2D correlation spectroscopy (COSY), total correlation spectroscopy (TOCSY), or selective spin-decoupling experiments, whereas $^{13}$C NMR assignments (Table III) were indicated by 2D heteronuclear single quantum correlation (HSQC), based on the $^1$H NMR assignments determined already. Inter-residue connectivities and further evidence for $^{13}$C assignments were gained from 2D heteronuclear multiple bond correlation (HMBC).

TABLE II $^1$H chemical shifts (ppm) of the galactose and glycerol residues of glycolipids and related compounds

| | BBGL-II | BBGL-II-Ac$_3$ | BBGL-III | BBGL-III-Ac$_4$ | MGDG$^a$ | 1,2-Dipalmitin$^b$ | Me-α-D-Galp (in D$_2$O) | Me-βP-D-Galp (in D$_2$O) |
|---|---|---|---|---|---|---|---|---|
| H-1' | 4.327 | 4.545 | 4.943 | 5.124 | 4.232 | | 4.846 | 4.323 |
| H-2' | ~3.617 | 5.184 | ~3.84 | 5.106 | 3.550 | | 3.836 | 3.509 |
| H-3' | ~3.617 | 5.024 | 3.770 | 5.317 | 3.502 | | 3.812 | 3.653 |
| H-4' | 3.877 | 5.370 | 4.096 | 5.460 | 3.896 | | 3.976 | 3.931 |
| H-5' | 3.666 | 3.886 | 3.807 | 4.203 | 3.510 | | 3.905 | 3.703 |
| H-6'a | 4.351, 4.346 | 4.191 | 3.927 | 4.107 | 3.829 | | 3.768 | 3.804 |
| H-6'b | 4.300, 4.294 | 4.101, 4.104 | ~3.82 | 4.075 | 3.757 | | 3.742 | 3.759 |
| OMe | | | | | | | 3.422 | 3.581 |
| OAc | | 2.142, 2.061, 1.982 | | 2.138, 2.071, 2.041, 1.988 | | | | |
| H-1''''a | | | 4.377 | 4.340 | 4.381 | 4.319 | | |
| H-1''''b | | | 4.128 | 4.147 | 4.229 | 4.238 | | |
| H-2'''' | | | 5.253 | 5.198 | 5.279 | 5.083 | | |
| H-3''''a | | | 3.840 | 3.816 | 3.954 | 3.751, 3.738 | | |
| H-3''''b | | | 3.634 | 3.620 | 3.723 | 3.724, 3.710 | | |
| HC=C | | | | 5.343 | | | | |

$^a$Commercially available "monogalactosyl diglyceride", mainly 1,2-di-O-stearoyl-3-O-β-D-galactopyranosyl glycerol.
$^b$1,2-di-O-palmitoyl glycerol

TABLE III $^{13}$C chemical shifts (ppm) of glycolipids and related compounds

| | BBGL-II MGDG acid | BBGL-II-Ac$_3$ Palmitic Oleic acid | Cholesterol 1,2-Dipalmitin (in D$_2$O) | BBGL-III Me-α-D-Galp (in D$_2$O) | BBGL-III-Ac$_4$ Me-β-D-Galp |
|---|---|---|---|---|---|
| C-1 (Chol) | 37.30 | 37.24 | 37.28 | | |
| C-2 | 38.89 | 38.98 | 31.38 | | |
| C-3 | 79.46, 79.45 | 80.40 | 72.80 | | |
| C-4 | 29.73 | 29.73 | 42.33 | | |
| C-5 | 140.37 | 140.35 | 140.78 | | |
| C-6 | 122.12 | 122.18 | 121.71 | | |

TABLE III-continued $^{13}$C chemical shifts (ppm) of glycolipids and related compounds

| | BBGL-II MGDG | BBGL-II-Ac$_3$ Palmitic Oleic | Cholesterol 1,2-Dipalmitin | BBGL-III Me-α-D-Galp | BBGL-III-Ac$_4$ Me-β-D-Galp |
|---|---|---|---|---|---|
| | acid | acid | (in D$_2$O) | (in D$_2$O) | |
| C-7 | 31.97 | 31.96 | 31.82 | | |
| C-8 | 31.89 | 31.89 | 31.68 | | |
| C-9 | 50.21 | 50.20 | 50.16 | | |
| C-10 | 36.75 | 36.74 | 36.51 | | |
| C-11 | 21.09 | 21.08 | 21.10 | | |
| C-12 | 28.24 | 28.24 | 28.24 | | |
| C-13 | 42.35 | 42.35 | 42.34 | | |
| C-14 | 56.79 | 56.78 | 56.79 | | |
| C-15 | 24.30 | 24.30 | 24.31 | | |
| C-16 | 39.80 | 39.78 | 39.80 | | |
| C-17 | 56.22 | 56.20 | 56.18 | | |
| C-18 | 11.07 | 11.87 | 11.87 | | |
| C-19 | 19.37 | 19.36 | 19.40 | | |
| C-20 | 35.80 | 35.80 | 35.80 | | |
| C-21 | 18.73 | 18.73 | 18.73 | | |
| C-22 | 36.22 | 36.21 | 36.21 | | |
| C-23 | 23.86 | 23.85 | 23.84 | | |
| C-24 | 39.54 | 39.54 | 39.53 | | |
| C-25 | 28.03 | 28.03 | 28.02 | | |
| C-26 | 22.57 | 22.57 | 22.57 | | |
| C-27 | 22.82 | 22.82 | 22.81 | | |
| C-1' (Gal) | 101.43 | 100.31 | | 99.32 | 96.62 |
| | 104.20 | | | 102.27 | 106.69 |
| C-2' | 71.90$^a$ | 69.18 | | 69.37 | 67.99 |
| | 71.40 | | | 72.33 | 73.59 |
| C-3' | 73.30$^a$ | 71.07 | | 70.88 | 67.50 |
| | 73.57 | | | 71.04 | 75.65 |
| C-4' | 68.35, 68.32 | 67.17, 67.15 | | 70.31 | 67.89 |
| | 68.98 | | | 72.08 | 71.54 |
| C-5' | 72.27, 72.25 | 70.69 | | 70.04 | 66.51 |
| | 75.25 | | | 73.59 | 78.00 |
| C-6' | 62.46, 62.42 | 61.27, 61.24 | | 63.06 | 61.61 |
| | 61.59 | | | 64.09 | 63.84 |
| OMe | | | | 57.88 | 60.02 |
| Ac(Me) | | 20.83, 20.69, | | | 20.70, 20.66 |
| | 20.61 | | | 20.65, 20.62 | |
| Ac(C=O) | | 170.36, 170.26, | | | 170.42, 170.32 |
| | 169.50 | | | 170.17, 169.95 | |
| C-1"(C=O) | 173.82$^b$ | 173.32$^c$ | | 173.59$^d$, | 173.27$^e$, |
| | | | | 173.56$^d$ | 173.24$^e$ |
| | 174.33, 174.03$^f$ | 179.82 | 173.79, 173.43 | | |
| C-2" | 34.27$^g$ | 34.08$^h$ | | 34.28 | 34.22$^j$ |
| | 34.48, 34.34 | 34.00 | 34.33, 34.14 | | |
| C-3" | 24.98$^k$ | 24.86 | | 24.90 | 24.90 |
| | 25.08 | 24.69 | 24.97, 24.92 | | |
| C-4"-C-13" | 29.77-29.18 | 29.79-29.12 | | 29.78-29.11 | 29.78-29.09 |
| | 29.88-29.29 | 29.69-29.08 | 29.72-29.12 | | |
| C-14" | 31.95 | 31.96 | | 31.94$^l$ | 31.94$^m$ |
| | 32.11 | 31.95 | 31.95 | | |
| C-15" | 22.70$^a$ | 22.70$^a$ | | 22.70 | 22.70 |
| | 22.86 | 22.69 | 22.71 | | |
| C-16" | 14.13 | 14.12 | | 14.12 | 14.12 |
| | 14.17 | 14.12 | 14.12 | | |
| C-1''' (C=O) | 173.80$^h$ | 173.29$^a$ | | 173.26$^d$ | 172.97$^e$ |
| | | 179.87 | | | |
| C-2''' | 34.24$^g$ | 34.05$^h$ | | 34.10 | 34.05$^j$ |
| | | 34.01 | | | |
| C-3''' | 24.95$^k$ | 24.86 | | 24.90 | 24.90 |
| | | 24.68 | | | |
| C-4'''-C-15''' | 29.77-29.18 | 29.79-29.12 | | 29.78-29.11 | 29.78-29.09 |
| | | 29.79-29.05 | | | |
| C-16''' | 31.95 | 31.96 | | 31.92$^l$ | 31.92$^m$ |
| | | 31.92 | | | |
| C-17''' | 22.71$^a$ | 22.60$^a$ | | 22.70 | 22.70 |
| | | 22.69 | | | |
| C-18''' | 14.13 | 14.12 | | 14.12 | 14.12 |
| | | 14.11 | | | |
| C-9''''=C-10'''' | 130.07, 129.70 | 130.03, 129.75 | | 130.06, 129.70 | 130.04, 129.71 |
| | | 130.04, 129.74 | | | |
| C-8''''—C=C, | 27.25$^p$ | 27.24 | | 27.24$^q$ | 27.24$^r$ |
| | | 27.24$^o$ | | | |
| C-11''''—C=C | 27.21$^p$ | 27.24 | | 27.20$^q$ | 27.20$^r$ |
| | | 27.17$^o$ | | | |

TABLE III-continued

| | | $^{13}$C chemical shifts (ppm) of glycolipids and related compounds | | | |
|---|---|---|---|---|---|
| | BBGL-II MGDG acid | BBGL-II-Ac$_3$ Palmitic Oleic acid | Cholesterol 1,2-Dipalmitin (in D$_2$O) | BBGL-III Me-α-D-Galp (in D$_2$O) | BBGL-III-Ac$_4$ Me-β-D-Galp |
| C-1'''' (Gro) | | | | 62.11 | 62.04 |
| | 63.04 | | 62.02 | | |
| C-2'''' | | | | 69.90 | 69.81 |
| | 70.56 | | 72.16 | | |
| C-3'''' | | | | 66.76 | 66.64 |
| | 63.06 | | 61.62 | | |

$^{a-e}$Assignments interchangeable.
$^f$The shifts in this group refer to stearoyl substituents, not to palmitoyl.
$^{g-r}$Assignments interchangeable.

The values of certain key homo- and hetero-nuclear coupling constants for the glycolipids are reported in Table IV. NMR data for several reference compounds or structural components of the glycolipids are also reported in Tables II-IV. Assignment of the $^{13}$C NMR resonances was further assisted by 1D distortionless enhancement by polarization transfer (DEPT) NMR spectrum editing experiments, in which carbon nuclei having different numbers of attached hydrogen atoms were distinguished.

TOCSY experiment also proved that the 1:2:1 triplet of 1:2:1 triplets at δ 3.553 is not part of the sugar proton spin system, and this multiplet was assigned to H-3 of the cholesterol moiety, particularly since it was also observed in a 1D TOCSY slice taken through the olefinic proton signals of BBGL-II. By integration, the latter signals amounted to ~2.5 protons in the 1D $^1$H NMR spectrum, due to coincidence of the single olefinic proton (H-6) signal of the cholesterol moiety with the olefinic proton signals of a proportion of unsat-

TABLE IV

Coupling constants (J, Hz) of galactopyranose and glycerol residues of glycolipid derivatives and related reference compounds

| | BBGL-II Solvent CDCl$_3$ | BBGL-II-Ac$_3$ CDCl$_3$ | BBGL-III CDCl$_3$ | BBGL-III-Ac$_4$ CDCl$_2$ | MGDG CDCl$_3$:CD$_3$OD (4:1 v/v) | 1,2-Dipalmitin CDCl$_3$ | Me-α-D-Galp D$_2$O | Me-β-D-Galp D$_2$O |
|---|---|---|---|---|---|---|---|---|
| J$_{1,2}$(Gal) | 7.5 | 8.0 | 3.8 | 3.7 | 7.3 | | 3.4 | 8.0 |
| J$_{2,3}$ | ND$^a$ | 10.5 | 9.8 | 10.0 | 9.7 | | 10.1 | 9.9 |
| J$_{3,4}$ | 3.2$^b$ | 3.5 | 3.2 | 3.5 | 3.3 | | 2.8 | 3.5 |
| J$_{5,6}$ | 1.0$^b$ | 1.0 | 1.1 | 1.1 | 1.1 | | 1.6 | 0.8 |
| J$_{5,6a}$ | 6.3 | 6.7 | 5.1 | 6.4 | 6.5 | | 6.8 | 7.9 |
| J$_{5,6b}$ | 7.2 | 6.7 | ND | 7.0 | 5.4 | | 5.5 | 4.4 |
| J$_{6a,6b}$ | 11.1 | 11.2 | 11.5 | 11.2 | 11.6 | | 11.7 | 11.7 |
| $^1$J$_{C-1',H-1'}$ | 158.7 | 157.4 | 170.5 | 172.4 | 160.2 | | 170.2 | 160.6 |
| J$_{1'''a,2'''b}$ (GRO) | | | 11.9 | 11.8 | 12.1 | 11.9 | | |
| J$_{1'''a,2'''}$ | | 4.1 | 4.1 | 3.2 | 4.5 | | | |
| J$_{1'''b,2'''}$ | | | 5.9 | 6.1 | 6.7 | 5.7 | | |
| J$_{2''',3'''a}$ | | | 4.8 | 4.3 | 5.4 | 4.8 | | |
| J$_{2''',3'''b}$ | | | 6.2 | 5.2 | 6.0 | 5.2 | | |
| J$_{3'''a,3'''b}$ | | | 10.9 | 11.2 | 10.9 | 12.2 | | |

$^a$Not determined
$^b$CD$_3$)$_2$CO:CDCl$_3$ (7:3) v/v solution.

Example 9

BBGL-II

The 1D $^1$H NMR spectrum of BBGL-II in chloroform-d solution was incompletely dispersed at 500 MHz, the H-2' and H-3' signals of the sugar residue being significantly overlapped at ~3.62 ppm.[1] Superimposition of the H-1', H-6'a, and H-6'b multiplets[2] was also observed, and a 1D slice taken through these signals in the 2D TOCSY spectrum yielded a subspectrum that contained all seven of the sugar chain proton signals (H-1'-H-6'b), presumably as two subsets comprised of the H-1'-H-4' and H-5'-H-6'b subgroups. Deshielding of the sugar methylene protons of the glycolipid by 0.55 ppm with respect to those of methyl β-D-galactopyranoside (Table II) suggests that O-6' of the sugar is acylated. This urated fatty acids in the isolated glycolipid. In support of this assignment, the TOCSY slice through the olefinic proton signals also contained a large number of multiplets in the aliphatic proton region (δ 2.8-0.9) due to connectivity to aliphatic protons of both cholesterol and unsaturated fatty acids.

[1]Cholesterol, galactose, palmitic acid, oleic acid, and glycerol residues are labeled as unprimed, and single, double, triple, and quadruple primed, respectively.
[2]For protons labeled as a and b, the a label refers to the proton that resonates at lower field, while the b label refers to the higher field proton.

Figure 3:
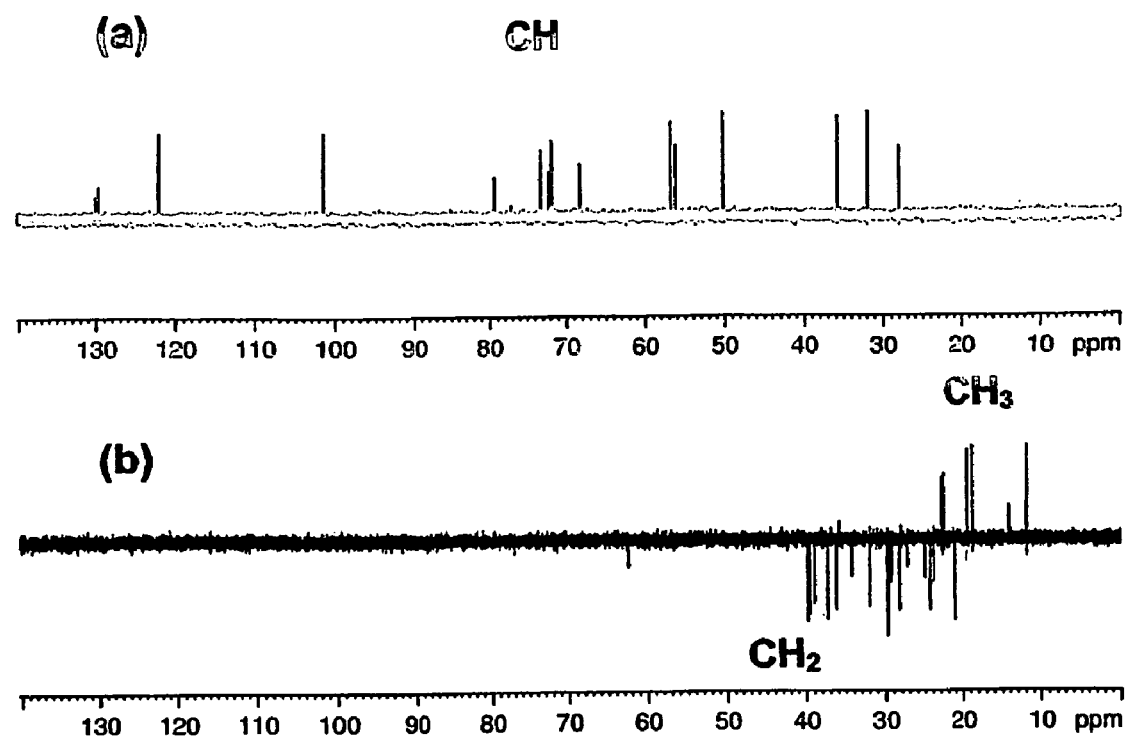
FIG. 3A-B are digital images of DEPT $^{13}$C NMR spectrum editing of the glycolipid BBGL-II in CDCl$_3$ at 126 MHz.

The $^{13}$C NMR spectrum of BBGL-II displayed 59 major, resolved resonances, of which five were due to quaternary $^{13}$C nuclei, i.e., not detected by $^{13}$C DEPT experiments. From low field to high field (Table III), the five quaternary $^{13}$C resonances were assigned as two ester carbonyl resonances, and C-5 (olefinic), C-13, and C-10 resonances of the cholesterol moiety. Of the total number of $^{13}$C resonances, 15 could be identified as CH by DEPT spectrum editing (FIG. 3a), together with 27 CH$_2$ and six CH$_3$ groups (FIG. 3b). Five of the CH$_3$ resonances were assigned to the cholesterol residue (Table III), and the sixth, weaker one at $\delta_C$ 14.13 to a combination of the signals of the ω methyl carbons of fatty acid ester groups, which typically may not be resolved from each other. The two major olefinic CH resonances at ~130 ppm were assigned to a predominant, unsaturated fatty acid ester group (oleic acid, 18:1), although additional weaker resonances in that region indicated the presence of minor proportions of other unsaturated fatty acid ester groups. The CH resonances at 122.12 and 79.46 ppm were assigned to C-6 and C-3 of the cholesterol moiety, respectively. Good agreement was obtained between the $^{13}$C chemical shifts of BBGL-II and those of its lipid components, cholesterol, palmitic acid, and oleic acid, except for nuclei near the points of attachment of the residues (Table III). The $^{13}$C assignments for cholesterol in chloroform-d solution are based on those reported (24) for a pyridine-d$_5$ solution, while ensuring that the assignments were consistent with the results of the DEPT experiments.

The remaining five CH resonances in the range 101.43-68.32 ppm were assigned to C-1'-C-5' of galactose, which also exhibited the CH$_2$ signal at 61.3 ppm (Table III). Doubling of the C4', C-5', and C-6' signals of galactose was observed, which could be attributed to the presence of two glycolipids bearing different fatty acid ester groups (palmitoyl and oleoyl) at O-6' of the galactose. The doubling of the cholesterol C-3 signal that was also observed is more difficult to explain in this way, since C-3 is more remote from the substituent at O-6' of the galactose than are C-4', C-5' and C-6'. This doubling may be due to rotational isomerism about the C-1'-O-1' bond (25).

The location of the cholesteryl group at O-1' of the galactose (Gal) residue in BBGL-II was indicated by the observation of an H-3/C-1'/cross peak in the 2D HMBC spectrum at 3.556/101.49 ppm. Similarly, the location of acyloxy group(s) at C-6' of the galactose was inferred from the observation of H-6'a/C=O and H-6'b/C=O cross peaks in the HMBC spectrum at 4.351/173.86 ppm and 4.297/173.86 ppm, respectively. Analysis of the cholesterol H-3 multiplet in the $^1$H NMR spectrum of BBGL-II yielded the coupling constants $J_{2eq,3}=J_{4eq,3}=4.7$ Hz, and $J_{2ax,3}=J_{4ax,3}=11.4$ Hz. These values define the orientation of H-3 as axial, and hence the oxygen atom (O-1') attached to C-3 is equatorial. Therefore, C-3 has the usual stereochemical configuration found in cholesterol. The NMR data for BBGL-II are consistent with a mixture of two structures, namely, 3-O-(6-O-palmitoyl-β-D-galactopyranosyl)cholesterol, and 3-O-(6-O-oleoyl-β-D-galactopyranosyl)cholesterol. Assignment of the sugar ring size was based on the similarity of the coupling constants of the sugar ring of BBGL-II to those of methyl β-D-galactopyranoside (Table IV). The anomeric configuration of BBGL-II is discussed below.

Example 10

Glycolipid BBGL-II-Ac$_3$

Figure 4:
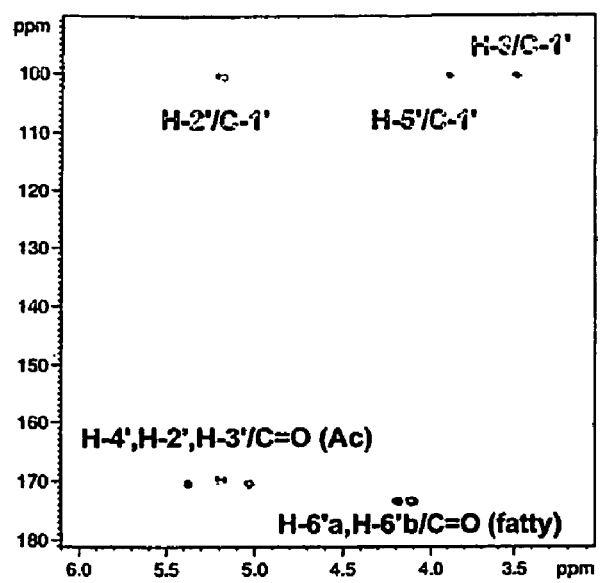
FIG. 4 shows the partial 2D $^1$H/$^{13}$C HMBC NMR spectrum of glycolipid BBGL-II-Ac$_3$ in CDCl$_3$ at 500/126 MHz, showing the inter-residue, $^1$H/$^{13}$C connectivities for the Gal $^1$H/acetyl carbonyl $^{13}$C, Gal $^1$H/fatty acid ester carbonyl $^{13}$C, and cholesterol H-3/Gal C-1' combinations. Two intra-residue connectivities are also shown.
Figure 5:
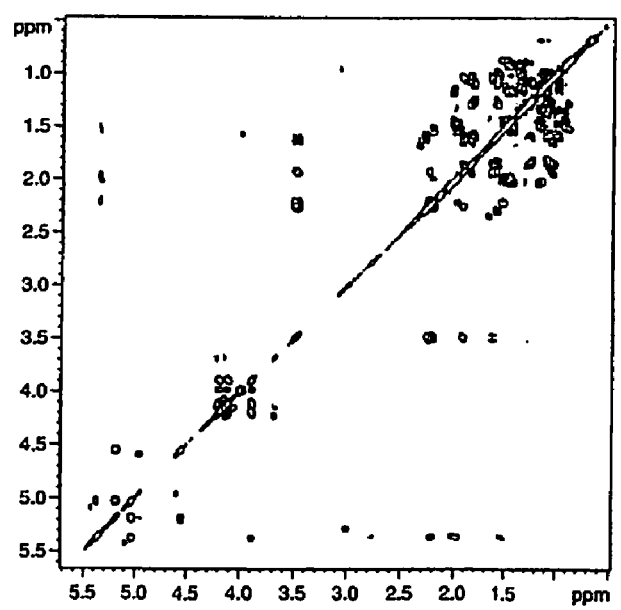
FIG. 5 shows the 2D $^1$H/$^1$H COSY-30 NMR spectrum of BBGL-II-Ac$_3$ in CDCl$_3$ at 500 MHz, showing vicinal and geminal $^1$H/$^1$H connectivities.

Convincing NMR evidence for the presence of galactose in BBGL-II was obtained by its peracetylation, which yielded a triacetyl derivative, the $^1$H NMR spectrum of which was better dispersed and resolved than that of BBGL-II. This spectrum showed the narrow H-4' quartet ($J_{3',4'}$ 3.5 Hz, $J_{4',5'}$ 1.0 Hz) that is characteristic of the galacto configuration, together with the wide quartets expected for H-2' and H-3'. All three of these signals were significantly deshielded (+1.41-1.57 ppm) with respect to their positions in non-acetylated BBGL-II (Table II), indicating that acetylation had occurred at HO-2', HO-3', and HO-4'. Confirmation of the positions of the three acetyl groups was obtained from the observation of 2D HMBC cross peaks between H-2', H-3', H-4' and three different $^{13}$C=O groups (FIG. 4). This spectrum also shows cross peaks between C-1' of Gal and H-3 of cholesterol, and between H-6'a/H-6'b of Gal and fatty acid ester C=O, thereby confirming the location of the cholesteryl group at O-1' of the Gal, and that of the fatty acyloxy residues at C-6'. The $^1$H signal assignments were confirmed by 2D COSY (see FIG. 5).

The large values $J_{1',2'}$ 7.5 Hz and 8.0 Hz observed for BBGL-II and BBGL-II-Ac$_3$, respectively (Table IV), indicate that H-1' and H-2' have the trans orientation in these glycolipids, and, therefore, that they have the β anomeric configuration. This was confirmed by measurement of the values $^1J_{C-1',H-1'}$ 158.7 Hz and 157.4 Hz for BBGL-II and BBGL-II-Ac$_3$, respectively (Table IV), which fall within the appropriate range for the β anomeric configuration (26), as exemplified by the value $^1J_{C-1',H-1}$ 160.6 Hz observed for methyl β-D-galactopyranoside (Me-β-D-Galp, Table IV).

The assignment of sugar ring size for BBGL-II and BBGL-II-Ac$_3$ was made on the basis of the similarity of the coupling constants of the sugar rings to those of methyl β-D-galactopyranoside (Table IV). Differences in the $J_{5',6'a}$ and $J_{5',6'b}$ values for BBGL-II and BBGL-II-Ac$_3$ on the one hand, and methyl β-D-galactopyranoside on the other may be attributed to different rotameric distributions about the C-5'-C-6' bond caused by the presence of a large substituent at O-6' of the glycolipids. The NMR data for BBGL-II-Ac$_3$ are consistent with its characterization as a mixture of 3-O-(2,3,4-tri-O-acetyl-6-O-palmitoyl-β-D-galactopyranosyl)cholesterol, and 3-O-(2,3,4-tri-O-acetyl-6-O-oleoyl-β-D-galactopyranosyl) cholesterol.

Example 11

BBGL-III

Figure 6:
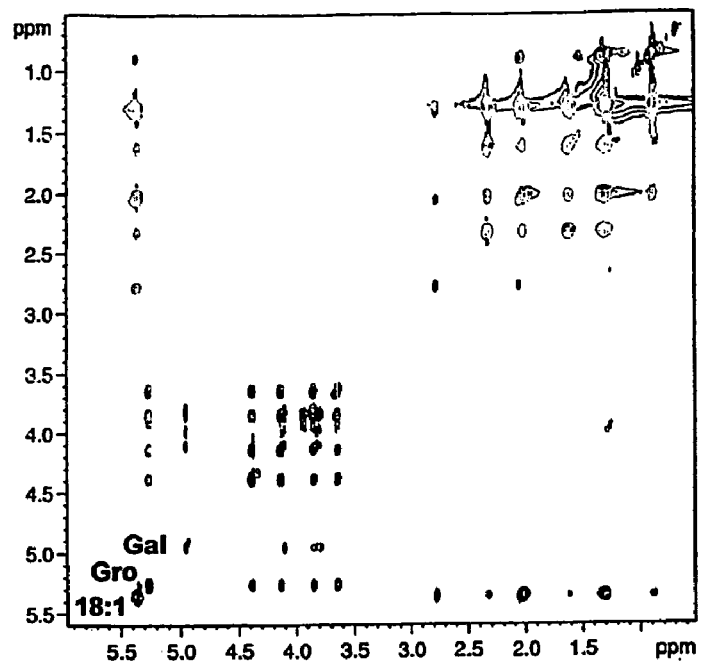
FIG. 6 shows the 2D $^1$H/$^1$H TOCSY NMR spectrum of glycolipid BBGL-III in CDCl$_3$ at 500 MHz. The characteristic Gal, Gro, and fatty acid 18:1 subspectra are identified.
Figure 7:
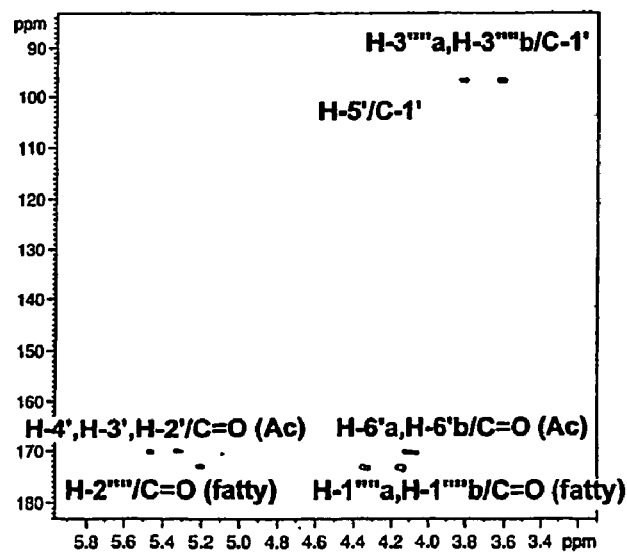
FIG. 7 shows a partial 2D $^1$H/$^{13}$C HMBC NMR spectrum of glycolipid BBGL-III-Ac$_4$ in CDCl$_3$ at 500/126 MHz, showing inter-residue $^1$H/$^{13}$C connectivities for four Gal protons with acetyl carbonyl $^{13}$C nuclei, three glyceryl protons with fatty acid ester carbonyl $^{13}$C nuclei, and two glyceryl protons with C-1' of Gal.

The $^1$H NMR spectrum of BBGL-III in chloroform-d solution was well dispersed; in particular, the glycerol protons are fully dispersed at 500 MHz, and both the 2D COSY spectrum and the 2D TOCSY spectrum (FIG. 6) contain five-multiplet strings that represent (from lower field to higher field) the glycerol protons H-2'''', H-1''''a, H-1''''b, H-3''''a, and H-3''''b. These 2D spectra have a similar appearance because H-2'''' is spin coupled to all of the other protons on the glycerol carbon chain, and therefore generates a string of cross peaks in the COSY spectrum that resembles that in the TOCSY spectrum. The latter spectrum (FIG. 5) also exhibits an H-1'-H-4' multiplet string that is characteristic of the galacto configuration, transmission of magnetization from H-4' to H-5', H-6'a, and H-6'b commonly being inhibited by the small magnitude of $J_{4',5'}$ (see Table IV). As a result, the H-4' multiplet of the Gal residue is characteristically narrow ($J_{3',4'}$ 3.2 Hz, $J_{4',5'}$ 1.1 Hz) A seven-multiplet string in the 2D TOCSY spectrum represents the mutual exchange of magnetization between the olefinic protons (δ 5.344) and the aliphatic protons in an unsaturated fatty acid (18:1).

The DEPT-135 $^{13}$C NMR spectrum of BBGL-III indicated six CH resonances and three CH$_2$ signals in the sugar region, consistent with the presence of one glycerol residue and one aldose residue, as well as 25 incompletely resolved CH$_2$ signals and one CH$_3$ resonance in the aliphatic carbon region that were assigned to fatty acids. Two strong resonances at $\delta_C$ 130.06 and 129.70 suggested the presence of one, predominant unsaturated fatty acid residue. However, the observation of two weaker pairs of signals in this olefinic carbon region indicated the presence of minor proportions of other unsaturated fatty acids. Three strong $^{13}$C resonances were observed in the C=O region (Table III), together with one weaker one. The substantial deshielding (+0.724, +0.567, and +1.470 ppm, respectively) of the H-1""a, H-1""b, and H-2"" protons of the glyceryl residue of BBGL-III with respect to the corresponding protons of the parent glycerol ($\delta_H$ in D$_2$O, 3.653, H-1""a; 3.561, H-1""b; 3.783, H-2"") pointed to acylation of O-1"" and O-2"" of the glyceryl residue (Table II). Confirmation of the positions of the acyl groups was provided by the observation of H-1""a/C=O, H-1""b/C=O, and H-2""/C=O cross peaks in the 2H HMBC spectrum of BBGL-III. This spectrum also displayed an H-3""b/C-1' cross peak, which locates the galactosyl residue at O-3"" of the glycerol moiety.

Example 12

BBGL-III-Ac$_4$

Peracetylation of BBGL-III yielded a product whose $^1$H and $^{13}$C NMR spectra exhibited four, intense acetyl methyl proton signals, and four acetyl methyl carbon and carbonyl carbon signals, respectively, indicating the formation of a tetra-O-acetyl derivative. Substantial deshielding (+1.266 to +1.547 ppm) of the Gal H-2', H-3', and H-4', and more limited deshielding (+0.180 to +0.255 ppm, Table II) of H-6'a and H-6'b pointed to acetylation of O-2', O-3', O-4', and O-6' of the Gal residue. This was confirmed by the detection of H-2'/C=O, H-3'/C=O, H-4'/C=O, H-6'a/C=O, and H-6'b/C=O cross peaks in the 2D HMBC spectrum of BBGL-III-Ac$_4$ (FIG. 6), in the case where the carbonyl carbon signals of the acetyl and fatty acid ester groups are readily differentiated by their $^{13}$C chemical shifts in the 170 ppm and 173 ppm regions, respectively (Table III). In the 173 ppm region, the 2D HMBC spectrum of BBGL-III-Ac$_4$ also displayed cross peaks of H-1""a, H-1""b, and H-2"" with fatty acid ester carbonyl carbons, together with an H-3""a/C-1' cross peak that supports the assigned location of the Gal residue at O-3"" of the glycerol unit.

The small values $J_{1',2'}$ 3.8 Hz and 3.7 Hz, respectively, for BBGL-III and BBGL-III-Ac$_4$ (see Table IV) indicate the gauche orientation for H-1' and H-2' in these derivatives, which means that their Gal residues have the α anomeric configuration. This was confirmed by the large values $J_{C-1',H-1'}$ 170.5 Hz and 172.4 Hz, respectively, for BBGL-III and BBGL-III-Ac$_4$ (Table IV), which fall within the range expected for α anomers (26), as was observed for methyl α-D-galactopyranoside (Me-α-D-Galp, Table IV).

The NMR data for BBGL-III are consistent with the structure 3-O-D-galactopyranosyl-1(2)-O-oleoyl-2(1)-O-palmitoyl-glycerol, and those for BBGL-III-Ac$_4$ support the structure 3-O-(2,3,4,6-tetra-O-acetyl-α-D-galactopyranosyl)-1(2)-O-oleoyl-2(1)-O-palmitoyl-glycerol. Again, the assignment of sugar ring size was based on the similarity of the sugar ring coupling constants to those of methyl α-D-galactopyranoside (Table IV).

Example 13

Monogalactosyl Diglyceride

The present inventors realized that commercially available monogalactosyl diglyceride (MGDG) is a close structural analog of BBGL-III, and this product was therefore studied as a reference compound, and to refine the analytical techniques described herein. The $^1$H NMR spectrum of MGDG was quite well dispersed at 500 MHz, and the seven spin multiplets originating from the Gal residue were readily recognized, including the narrow H-4' quartet ($J_{3',4'}$ 3.3 Hz, $J_{4',5'}$ 1.1 Hz) that is characteristic of the galacto configuration. Moreover, the ring proton coupling constants (Table IV) indicate that the galactose residue is present as a pyranosyl ring, in concert with the glycolipid derivatives discussed earlier. No olefinic proton signals were observed for MGDG.

The 2D COSY and TOCSY $^1$H NMR spectra of MGDG contained the same highly dispersed, five-multiplet strings that are characteristic of a glycerol residue bearing acyloxy groups at C-1"" and C-2"", a substitution pattern that is supported by the downfield shifts of H-1""a, H-1""b, and H-2"" (Table II). DEPT-135 $^{13}$C NMR spectra exhibited six main CH resonances and three predominant CH$_2$ signals in the sugar region (Gal+Gro), together with 14 resolved CH$_2$ signals and one CH$_3$ resonance in the aliphatic region that represent two fatty acid ester residues, as was confirmed by the detection of two C=O signals at $\delta_C$ 174.31 and 174.01 in the normal $^{13}$C NMR spectrum. The location of the acyloxy groups at C-1"" and C-2"" is substantiated by the observation of H-1""a/C=O, H-1""b/C=O, and H-2""/C=O cross peaks in the 2D HMBC spectrum of MGDG. This spectrum also displayed H-3""a/C-1' and H-3""b/C-1' cross peaks that confirm the linkage of C-1' of the Gal residue to O-3"" of the glycerol moiety. Good agreement between the $^{13}$C chemical shifts of all three of the glyceryl carbons was obtained for MGDG, BBGL-III, and BBGL-III-Ac$_4$ (see Table III), but for 1,2-dipalmitin, the C-3"" shift is substantially upfield of the corresponding shifts for the other compounds, owing to the lack of a deshielding glycosyl substituent in this diglyceride.

The large value $J_{1',2'}$ 7.3 Hz and small value $J_{C-1',H-1'}$ 160.2 Hz (Table IV) prove that MGDG has the β anomeric configuration, i.e., the opposite configuration to the glycolipid BBGL-III. Taken together, the NMR and GC-MS data for MGDG indicate that it consists mainly of 1,2-di-O-stearoyl-3-O-β-D-galactopyranosyl glycerol, although weaker peaks in the NMR and GC-MS spectra indicated the presence of minor proportions of other components. The diastereomeric relationship of MGDG and BBGL-III and lack of an unsaturated fatty acid residue in MGDG is sufficient to cause these two glycolipids to have different solubilities. In contrast to all of the other lipids studied, dissolution of MGDG in CDCl$_3$ required the addition of about 20% CD$_3$OD.

Figure 8:
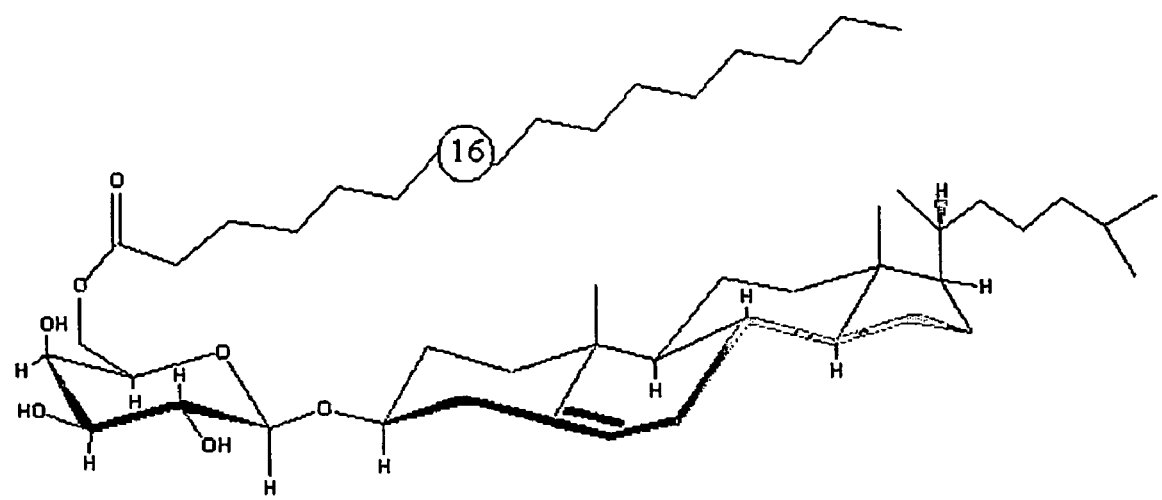
FIG. 8 is a diagram of the structure of the main fraction of native BBGL-II, cholesteryl 6-O-palmitoyl-b-d-galactopyranoside.
Figure 9:
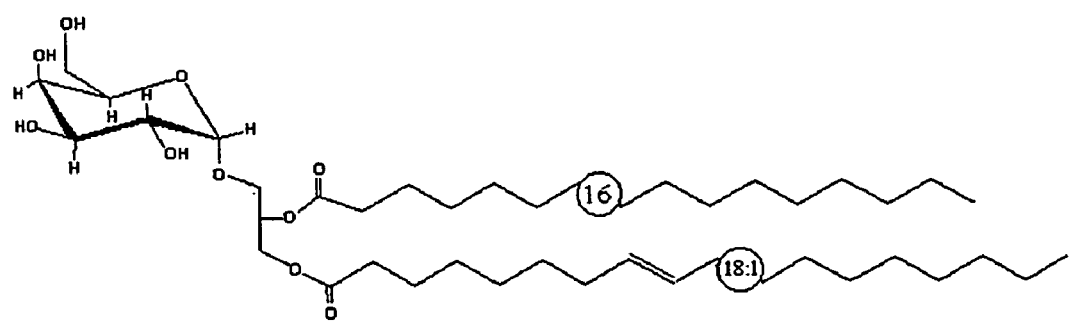
FIG. 9 is a diagram of the structure of the main fraction of native BBGL-II, I-oleil, 2-palmitoyl, 3-[O-α-D-galactopyranosyl]-sn-glycerol.

Thus, BBGL-II and BBGL-III were isolated from *B. burgdorferi* strains B31, N40 and BL303 (15), and purified to near homogeneity by silica gel chromatography. Using various analytical procedures (GLC, MALDI-TOF, FAB, and NMR spectrometry), the structure of the major polar membrane glycolipids of *B. burgdorferi* have been identified as cholesteryl 6-O-acyl-β-D-galactopyranoside (BBGL-II, FIG. 8), and 1,2-diacyl-3-[O-α-D-galactopyranosyl]-sn-glycerol (BBGL-III, FIG. 9).

BBGL-III shows high structural homology to BOLIP-7, a monogalactosyl diacyl glycerol previously described. However, the results obtained clearly demonstrate that the terminal galactose moiety in BBGL-II is indeed linked to cholesterol, unlike BBGL-III, in which the galactose is linked to glycerol.

Further evidence of the cholesterol moiety in BBGL-II was obtained by metabolic labeling of this glycolipid upon cultivation of the cells with $^{14}$C-cholesterol. In these experiments, 80% of the radioactivity in the total lipid fraction could be attributed to BBGL-II. No significant amount of free cholesterol was detected in these experiments, suggesting the absence of free cholesterol from the pool of membrane lipids, and its rapid incorporation into BBGL-II. Free cholesterol, or cholesterol esters were shown to be incorporated in bacteria membranes in many species including Mycoplasma, *Helicobacter pylori, Micrococcus lysodeikticus, Bacillus megaterium*, and *Proteus mirabilis*. However, de-novo synthesized cholesteryl glucosides, in which cholesterol is incorporated from the growth media to be linked to sugar and/or lipid moieties, has been demonstrated thus far only in Mycoplasmas, *Helicobacter pylori*, and *B. hermsi*, for all of which, the carbohydrate being Glucose. Previous studies have demonstrated that cholesterol is a highly immunogenic molecule. The abundance of cholesterol-containing BBGL-III in *B. burgdorferi* membranes can therefore, result in elevated titers of anti cholesterol antibodies during Lyme disease pathogenesis.

Polymyxin B, a polycationic cyclic peptide, has been used as affinity sorbent for the removal of endotoxins, mainly LPS and lipid A. When sonicated *B. burgdorferi* cells were loaded on a column containing immobilized polymixin B, the presence of BBGL-II could be demonstrated in the bound material after elution with deoxycholate. It is interesting to note, that BBGL-III was not bound to the column under the same conditions. The driving force of the binding of endotoxins to polymixin B are hydrophobic interactions between these two structures. It is likely to assume that some structural elements of BBGL-II present characters similar to that of lipid A.

The molecular mimicry of lipid A by BBGL-II has also been demonstrated by triggering the secretion of proinflammatory mediators such as interleukin-1, IL-6, TNF-alpha, and $PGE_2$ upon stimulation of cell cultures with various *B. burgdorferi* preparations containing BBGL-II. Without being bound by theory, it is therefore likely that BBGL-II acts as a "functional LPS" in *B. burgdorferi*.

Example 14

Immunologic Results

Specific antibodies were induced in mice and rabbits injected with various formulations of the compound of formula B (BBGL-II) (see FIGS. 10 and 11). BBGL-III induced antibodies, mostly IgM, that reacted with both glycolipids (data not shown). BBGL-II in PBS (likely as micelles) was more immunogenic than as a solute in DMSO or squalene. Highest titers were obtained with Freund's adjuvant.

Surprisingly, despite its small size, BBGL-II elicited antibodies in mice and rabbits, mostly of the IgM isotype. These antibodies were specific to the homologous glycolipid. In contrast, BBGL-III elicited antibodies that reacted with both glycolipids.

Example 15

Synthesis of a BBGL-II Analog ("Azido BBGL-II")

The target compound ("azido BBGL-II", compound 19, see FIG. 15) differs from the native glycolipid BBGL-II in that it contains an azido group at the terminus of the palmitoyl group in place of a proton. The synthesis of 19 was achieved from major intermediates galactosyl bromide 4, cholesterol 5 and ω-azidopalmitic acid 16.

Figure 12:
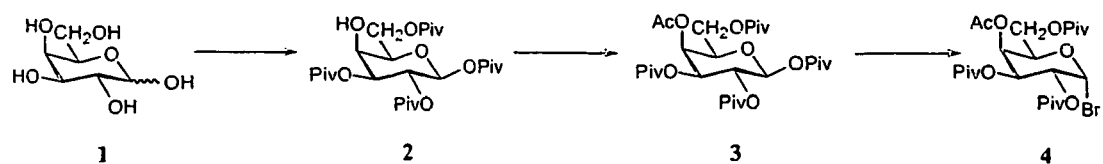
FIGS. 12-15 depict a synthesis scheme for making an example of a synthetic lipid described herein.
Figure 13:
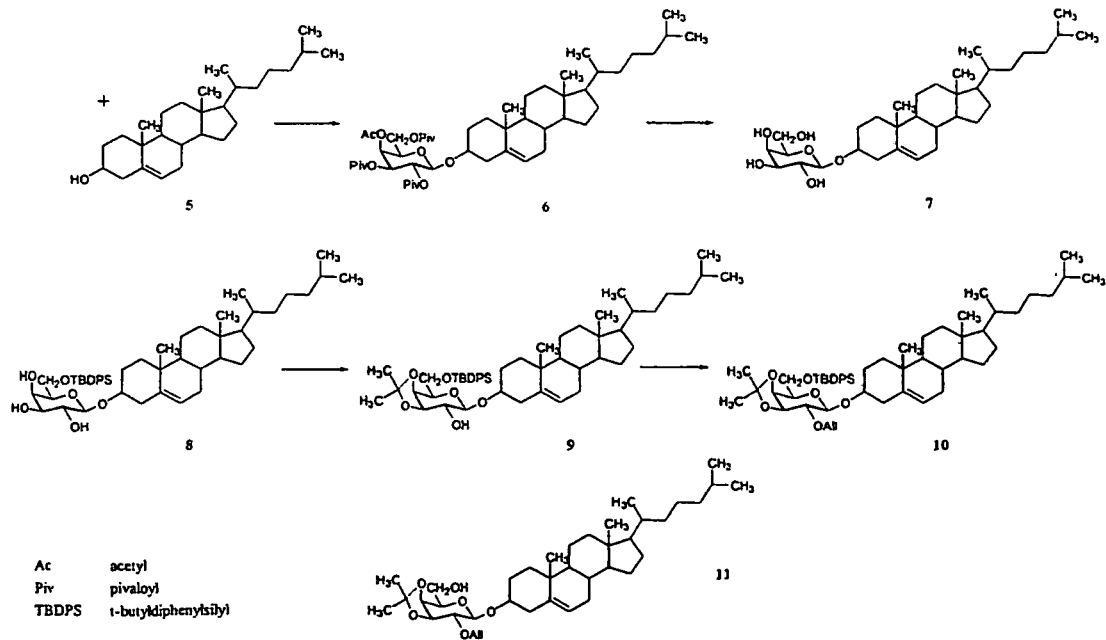

Compound 4 (see FIG. 12) was prepared from galactose 1 that was treated with pivaloyl chloride in pyridine. Instead of the expected penta-pivaloyl derivative, the partially pivaloylated compound 2 was obtained in good yield and high purity without the need of chromatographic purification. The free hydroxyl group in compound 2 was protected by an acetyl group (→3). This was followed by treatment with hydrogen bromide in acetic acid to provide the galactosyl bromide 4. Bromide 4 was coupled with cholesterol 5 under promotion by silver trifluoromethanesulfonate in dichloromethane to provide the desired β-galactosyl-cholesterol 6 in a stereoselective manner (see FIG. 13). The β-anomeric configuration was demonstrated by 1-H NMR spectroscopy. The O-protecting groups were subsequently removed by treatment with sodium methoxide in a mixture of anhydrous dichloromethane and methanol to provide the cholesteryl β-D-galactopyranoside 7 as an amorphous solid.

Numerous protecting group combinations were tried to allow the introduction of the pivaloyl moiety in to HO-6 position of the tetraol 7. In our experience, the use of acyl-type protecting groups including acetyl, levulinoyl, chloroacetyl groups proved largely unsuccessful because of the uncontrollable migration of these groups within the galactose moiety. Eventually, this problem was overcome by using a combination of allyl, isopropylidene, and silyl protecting groups. Thus, the primary hydroxyl group in 7 was protected with a t-butyl-diphenylsilyl group to afford compound 8 without affecting the other hydroxyls. Next, the triol 8 was treated with dimethoxypropane in the presence of camphorsulfonic acid to introduce an isopropylidene group to HO-3 and HO-4 to afford compound 9. Subsequently, intermediate 9 was treated with allyl bromide/NaH in dimethylformamide to afford the fully protected derivative 10 from which the silyl protecting group was selectively removed without affecting other parts of the molecule to provide compound 11. This derivative features the free HO-hydroxyl group that is the point of attachment for the palmitoyl moiety.

Figure 14:
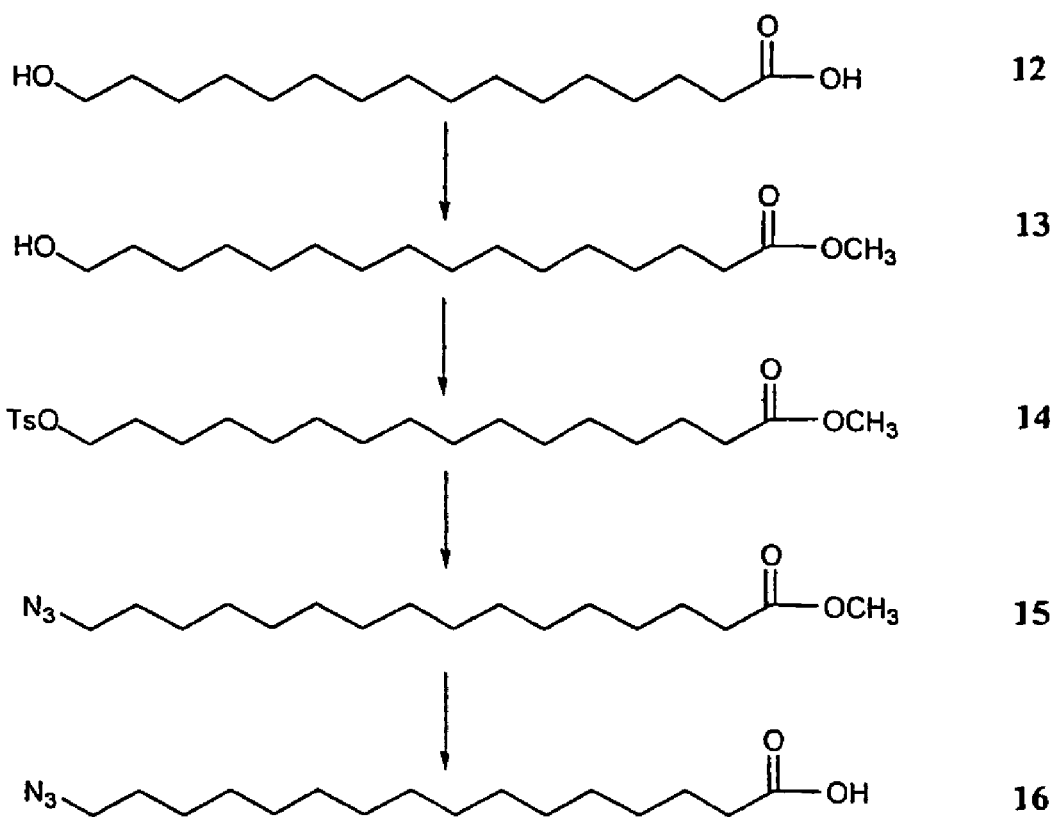

Synthesis of the 16-azidopalmitic acid intermediate 16 is shown in FIG. 14. Thus, commercially available 16-hydroxypalmitic acid 12 was treated with diazomethane to afford methyl ester 13 in a quantitative yield. Next, the alcohol 13 was treated with p-toluenesulfonyl chloride in pyridine to afford sulfonate 14 which was subsequently treated with sodium azide in dimethylformamide to afford the azido-ester 15. Next, the methyl ester was cleaved with potassium hydroxide in a mixture of dioxane and water to afford the acid 16.

Figure 15:
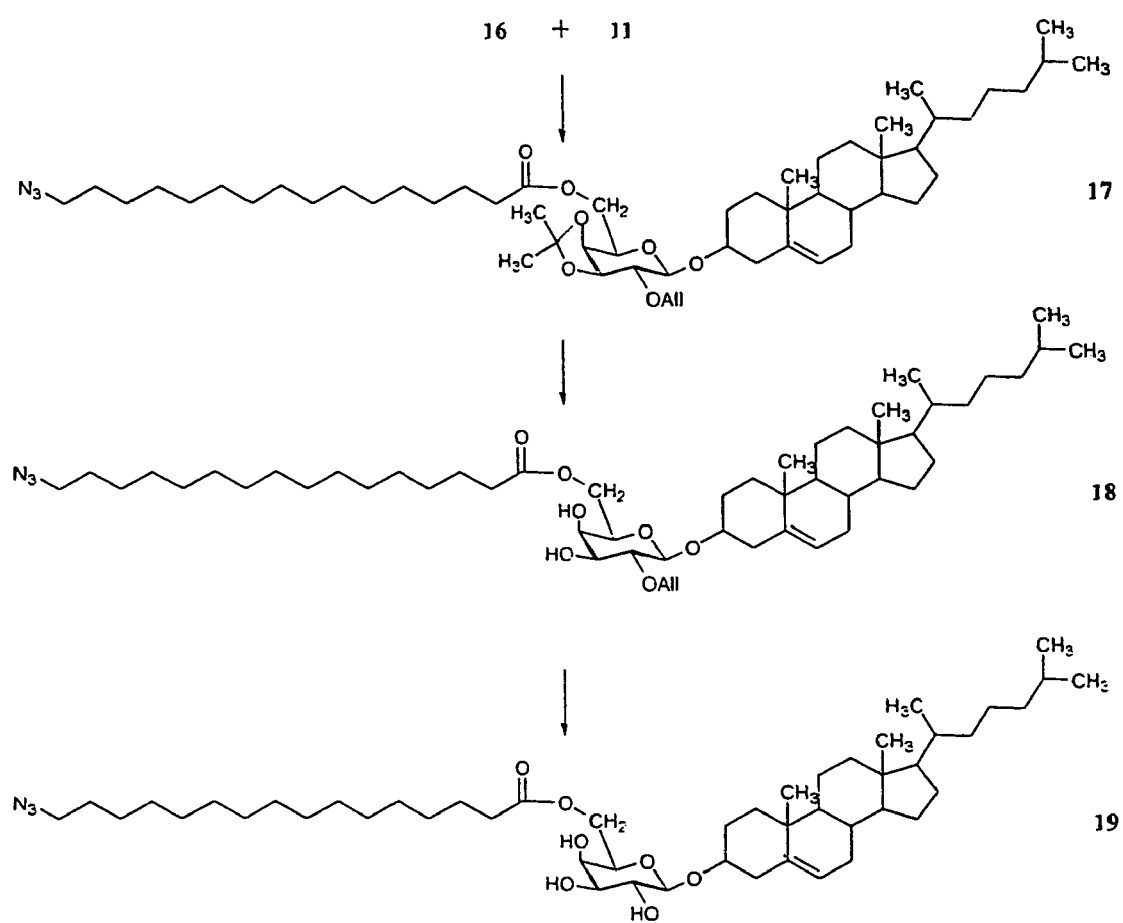

Cholesteryl palmitoyl-galactopyranoside 19 was prepared by condensation of compound 11 with the azidopalmitic acid 16 in the presence of dicyclohexylcarbodiimide in ethyl acetate in a quantitative yield (~17) (see FIG. 15). Subsequently, the protecting groups were removed in two steps. First, compound 17 was treated with acetic acid/water to remove the isopropylidene group to afford the diol 18. This was followed by treatment of 18 with the iridium complex $(MePh_2)_2(C_8H_{12})IrPF_6$ in tetrahydrofuran and oxidative removal of the resulting propenyl group using a combination of osmium tetroxide and trimethylamine N-oxide to afford the azide 19 as an amorphous solid.

ELISA and TLC overlay assays demonstrated that antibodies were raised against the synthetic compound 19 to the same extent as with the purified native BBGL-II.

It will be apparent that the precise details of the methods or compositions described may be varied or modified without departing from the spirit of the described invention. We claim all such modifications and variations that fall within the scope and spirit of the claims below.

REFERENCES

Reference List

1. Orloski, K. A., Hayes, E. B., Campbell, G. L., and Dennis, D. T. (2000) *MMWR CDC Surveill Summ.* 49, 1-11
2. Steere, A. C. (2001) *N. Engl. J. Med.* 345, 115-125
3. Sadziene, A. and Barbour, A. G. (1996) *Infection* 24, 195-202
4. Rahn, D. W. (2001) *Infect. Dis. Clin. North Am.* 15, 171-187
5. Lathrop, S. L., Ball, R., Haber, P., Mootrey, G. T., Braun, M. M., Shadomy, S. V., Ellenberg, S. S., Chen, R. T., and Hayes, E. B. (2002) *Vaccine* 20, 1603-1608
6. Vinh, T. U., Shi, M. H., Adler, B., and Faine, S. (1989) *J. Gen. Microbiol.* 135 (Pt 10), 2663-2673
7. Halter, M. R. and Joens, L. A. (1988) *Infect. Immun.* 56, 3152-3156
8. Takayama, K., Rothenberg, R. J., and Barbour, A. G. (1987) *Infect. Immun.* 55, 2311-2313
9. Cinco, M., Banfi, E., Balanzin, D., Godeas, C., and Panfili, E. (1991) *FEMS Microbiol. Immunol.* 3, 33-38
10. Eiffert, H., Lotter, H., Jarecki-Khan, K., and Thomssen, R. (1991) *Med. Microbiol. Immunol. (Berl)* 180, 229-237
11. Wheeler, C. M., Garcia Monco, J. C., Benach, J. L., Golightly, M. G., Habicht, G. S., and Steere, A. C. (1993) *J. Infect. Dis.* 167, 665-674
12. Radolf, J. D., Goldberg, M. S., Bourell, K., Baker, S. I., Jones, J. D., and Norgard, M. V. (1995) *Infect. Immun.* 63, 2154-2163
13. Hossain, H., Wellensiek, H. J., Geyer, R., and Lochnit, G. (2001) *Biochimie* 83, 683-692
14. Bligh, E. G. and Dyer, W. J. (1969) *Can. J. Biochem. Physiol.* 37, 911-917
15. Ben Menachem, G., Wagner, F., Zahringer, U., Rietschel, E. T., and Rottem, S. (1997) *FEMS Microbiol. Lett.* 154, 363-369
16. Sawardeker, J. S., Sloneker, J. H., and Jeanes, A. (1965) *Biochem. J.* 37, 1602-1604
17. Fay, L. and Richli, U. (1991) *J. Chromatography* 541, 89-98
18. Rasley, A., Anguita, J., and Marriott, I. (2002) *J. Neuroimmunol.* 130, 22-31
19. Roth, h., Segal, S., and Bertoli, D. (1965) *Anal. Biochem.* 10, 32-52
20. Pasciak, M., Ekiel, I., Grzegorzewicz, A., Mordarska, H., and Gamian, A. (2002) *Biochim. Biophys. Acta* 1594, 199-205
21. Dell, A. (1987) *Adv. Carbohydr. Chem. Biochem.* 45, 19-72
22. Zahringer, U., Wagner, F., Rietschel, E. T., Ben Menachem, G., Deutsch, J., and Rottem, S. (1997) *J. Biol. Chem.* 272, 26262-26270
23. Ciucanu, I. and Kerek, F. (1984) *Carbohydr. Res* 131, 209-217
24. Reich, H. J., Jautelat, M., Messe, M. T., Weigert, F. J., and Roberts, J. D. (1969) *Journal of the American chemical society* 91, 7445-7453
25. Hirai, Y., Haque, M., Yoshida, T., Yokota, K., Yasuda, T., and Oguma, K. (1995) *J. Bacteriol.* 177, 5327-5333
26. Bock, K. and Pedersen, C. (1975) *Acta Chemica Scandinavica B* 29, 258-264
27. Honarvar, N., Schaible, U. E., Galanos, C., Wallich, R., and Simon, M. M. (1994) *Immunology* 82, 389-396
28. Beck, G., Benach, J. L., and Habicht, G. S. (1990) *Biochem. Biophys. Res Commun.* 167, 89-95
29. Beck, G., Habicht, G. S., Benach, J. L., and Coleman, J. L. (1985) *J. Infect. Dis.* 152, 108-117
30. Habicht, G. S., Beck, G., Benach, J. L., and Coleman, J. L. (1986) *Zentralbl. Bakteriol. Mikrobiol. Hyg. [A]* 263, 137-141
31. Rottem, S. (2002) *Biochem. Biophys. Res. Commun.* 292, 1289-1292
32. Razin, S. (1975) *J. Bacteriol.* 124, 570-572
33. Mayberry, W. R. and Smith, P. F. (1983) *Biochim. Biophys. Acta* 752, 434-443
34. Livermore, B. P., Bey, R. F., and Johnson, R. C. (1978) *Infect. Immun.* 20, 215-220
35. Alving, C. R. and Swartz, G. M., Jr. (1991) *Crit Rev. Immunol.* 10, 441-453
36. Anspach, F. B. (2001) *J. Biochem. Biophys. Methods* 49, 665-681
37. Srimal, S., Surolia, N., Balasubramanian, S., and Surolia, A. (1996) *Biochem. J.* 315 (Pt 2), 679-686
38. Habicht, G. S., Beck, G., Benach, J. L., Coleman, J. L., and Leichtling, K. D. (1985) *J. Immunol.* 134, 3147-3154

The invention claimed is:

1. A compound of formula A below, or a pharmaceutically acceptable salt thereof, wherein the compound of formula A comprises

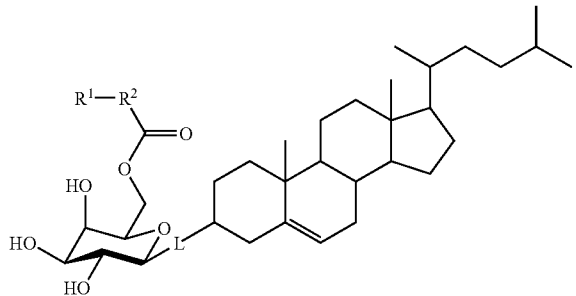

wherein $R^1$ is azido;

$R^2$ is a saturated carbon chain containing 5 to 20 carbon atoms; and

L is O.

2. A conjugate comprising the compound of formula A of claim 1 and at least one protein carrier, wherein the compound of formula A is covalently bound to the protein carrier.

3. The conjugate of claim 2, wherein the compound of formula A is covalently bound to the protein carrier via the R1 group.

4. The conjugate of claim 2, wherein the protein carrier comprises bovine serum albumin, ovalbumin, keyhole limpet hemocyanin, purified protein derivative of tuberculin, tetanus toxoid, cholera toxoid, diphtheria toxoid, *Pseudomonas aeruginosa* toxoid, *Clostridium* toxoid, Shiga toxin, hepatitis B antigen, or a sequence of amino acids of a *Borrelia burgdorferi* polypeptide.

5. A pharmaceutical composition comprising a therapeutically effective amount of the compound of claim 1 and a pharmaceutically acceptable carrier.

6. A pharmaceutical composition comprising a therapeutically effective amount of the conjugate of claim 2.

7. A compound, or a pharmaceutically acceptable salt thereof, having a structure represented by the formula:

8. A conjugate comprising the compound of claim 7 and at least one protein carrier, wherein the compound of claim 7 is covalently bound to the protein carrier.

9. A method of inducing an immune response to *B. burgdorferi* in a subject, comprising administering a therapeutically effective amount of the compound of claim 7 to the subject, thereby inducing the immune response.

10. The compound of claim 1, $R^2$ is a saturated carbon chain containing 11, 13, 15 or 17 carbon atoms.

11. A method of inducing an immune response to *B. burgdorferi* in a subject, comprising administering a therapeutically effective amount of the conjugate of claim 8 to the subject, thereby inducing the immune response.

12. A pharmaceutical composition comprising a therapeutically effective amount of the compound of claim 7.

* * * * *

UNITED STATES PATENT AND TRADEMARK OFFICE
CERTIFICATE OF CORRECTION

PATENT NO. : 7,666,846 B2 Page 1 of 1
APPLICATION NO. : 10/550907
DATED : February 23, 2010
INVENTOR(S) : Ben-Menachem et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 757 days.

Signed and Sealed this

Seventh Day of December, 2010

David J. Kappos
*Director of the United States Patent and Trademark Office*